US012589191B2

(12) United States Patent
Doyle et al.

(10) Patent No.: US 12,589,191 B2
(45) Date of Patent: Mar. 31, 2026

(54) DETERMINING A VOLUME OF A CONTAINER FOR DIALYSIS TREATMENT

(71) Applicant: Fresenius Medical Care Holdings, Inc., Waltham, MA (US)

(72) Inventors: Matthew J. Doyle, Concord, CA (US); Robert Zimmerman, Waltham, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1012 days.

(21) Appl. No.: 17/563,458

(22) Filed: Dec. 28, 2021

(65) Prior Publication Data

US 2023/0201432 A1      Jun. 29, 2023

(51) Int. Cl.
    *A61M 1/16*        (2006.01)
    *G01F 9/00*        (2006.01)
    (Continued)

(52) U.S. Cl.
    CPC ........ *A61M 1/1605* (2014.02); *A61M 1/1668* (2014.02); *G01F 9/008* (2013.01); *G01F 22/02* (2013.01); *A61M 2205/3303* (2013.01); *A61M 2205/3331* (2013.01); *A61M 2205/3334* (2013.01); *A61M 2205/3396* (2013.01); *A61M 2205/502* (2013.01); *G08B 21/182* (2013.01)

(58) Field of Classification Search
    None
    See application file for complete search history.

(56)            References Cited

U.S. PATENT DOCUMENTS 4,386,634  A      6/1983   Stasz et al.
5,486,286  A      1/1996   Peterson
                  (Continued)

FOREIGN PATENT DOCUMENTS

CN        104023763       9/2014
EP          2035059       3/2009
                  (Continued)

OTHER PUBLICATIONS

International Search Report and Written Opinion in Appln. No. PCT/US2022/053387, mailed Mar. 21, 2023, 12 pages.
                  (Continued)

*Primary Examiner* — Jonathan M Peo
(74) *Attorney, Agent, or Firm* — Fish & Richardson P.C.

(57)            ABSTRACT

A method includes receiving, by a processor of a dialysis machine, a dialysate flow rate, a bicarbonate setting value, a signal from a pressure sensor configured to measure a pressure within a container, and a signal indicating a state of a fill valve; determining, based on the signal received from the pressure sensor and the state of the fill valve, fill parameters; determining a volume of the container based on at least two of the fill parameters; determining a depletion time in which the concentrate will be depleted from the container based on the volume of the container, the dialysate flow rate, and the bicarbonate setting value; determining, based on the depletion time, an amount of time remaining before the concentrate will be depleted from the container; and causing the dialysis machine to indicate the amount of time remaining before the concentrate will be depleted from the container.

30 Claims, 14 Drawing Sheets

(51) Int. Cl.
  *G01F 22/02*          (2006.01)
  *G08B 21/18*          (2006.01)

(56)          References Cited

U.S. PATENT DOCUMENTS

| | | | |
|---|---|---|---|
| 5,902,476 | A | 5/1999 | Twardowski |
| 10,369,261 | B2 | 8/2019 | Jonas et al. |
| 10,668,199 | B2 | 6/2020 | Rada et al. |
| 11,123,464 | B2 | 9/2021 | Yuds et al. |
| 2006/0054215 | A1 | 3/2006 | Remkes et al. |
| 2008/0015487 | A1 | 1/2008 | Szamosfalvi et al. |
| 2010/0010426 | A1 | 1/2010 | Childers et al. |
| 2010/0010428 | A1 | 1/2010 | Yu et al. |
| 2010/0069817 | A1* | 3/2010 | Falkvall .................. B01F 25/50 |
| | | | 604/416 |
| 2013/0049974 | A1* | 2/2013 | Crnkovich .......... A61M 1/1662 |
| | | | 340/657 |
| 2013/0248426 | A1 | 9/2013 | Pouchoulin |
| 2014/0220699 | A1 | 8/2014 | Pudil |
| 2014/0263064 | A1* | 9/2014 | Jones ................ A61M 1/36222 |
| | | | 73/61.41 |
| 2015/0034536 | A1 | 2/2015 | Rada et al. |
| 2015/0034557 | A1 | 2/2015 | Pouchoulin |
| 2016/0101278 | A1 | 4/2016 | Norris et al. |
| 2016/0216150 | A1 | 7/2016 | Groeber et al. |
| 2017/0224897 | A1 | 8/2017 | Kopperschmidt |
| 2017/0265793 | A1 | 9/2017 | Maierhofer |
| 2017/0304519 | A1 | 10/2017 | Jonas et al. |
| 2017/0319768 | A1 | 11/2017 | Szpara et al. |
| 2017/0326284 | A1 | 11/2017 | Dulsner et al. |
| 2018/0093027 | A1 | 4/2018 | Oppegard et al. |
| 2019/0388600 | A1* | 12/2019 | Yuds .................. A61M 1/1601 |
| 2020/0061273 | A1 | 2/2020 | Hogard et al. |
| 2020/0179583 | A1 | 6/2020 | Hobot et al. |
| 2020/0294676 | A1 | 9/2020 | Cherif |
| 2022/0001086 | A1 | 1/2022 | Yuds et al. |
| 2024/0123127 | A1 | 4/2024 | Rovatti |
| 2025/0018098 | A1 | 1/2025 | Crnkovich et al. |
| 2025/0018099 | A1 | 1/2025 | Crnkovich et al. |

FOREIGN PATENT DOCUMENTS

| | | |
|---|---|---|
| EP | 3335742 | 6/2018 |
| WO | WO 2007/144427 | 12/2007 |
| WO | WO 2020/076945 | 4/2020 |

OTHER PUBLICATIONS

Glickman et al., "Choosing home hemodialysis for end-stage kidney disease," Feb. 7, 2023, retrieved on Sep. 14, 2023, retrieved from URL <https://www.uptodate.com/contents/home-hemodialysis>, 1 page.

UnitedHealthcare, "Home Hemodialysis (for North Carolina Only)," Jul. 1, 2023, retrieved on Sep. 14, 2023, retrieved from URL <https://www.uhcprovider.com/content/dam/provider/docs/public/policies/medicaid-comm-plan/nc/home-hemodialysis-nc-cs.pdf>, 11 pages.

Weinhandl, "Standardized Kt/V on Home Hemodialysis: Does It Matter?," Apr. 23, 2018, retrieved on Sep. 14, 2023, retrieved from URL <https://advancingdialysis.org/standardized-kt-v-home-hemodialysis-matter/>, 3 pages.

International Search Report and Written Opinion in International Appln. No. PCT/US2024/036779, mailed Oct. 14, 2024, 19 pages.

International Preliminary Report on Patentability in International Appln. No. PCT/US2019/037424, mailed Dec. 30, 2020, 7 pages.

International Search Report and Written Opinion in Appln. No. PCT/US2019/037424, dated Sep. 10, 2019, 9 pages.

International Preliminary Report on Patentability in International Appln. No. PCT/US2022/053387, mailed Jul. 11, 2024, 7 pages.

* cited by examiner

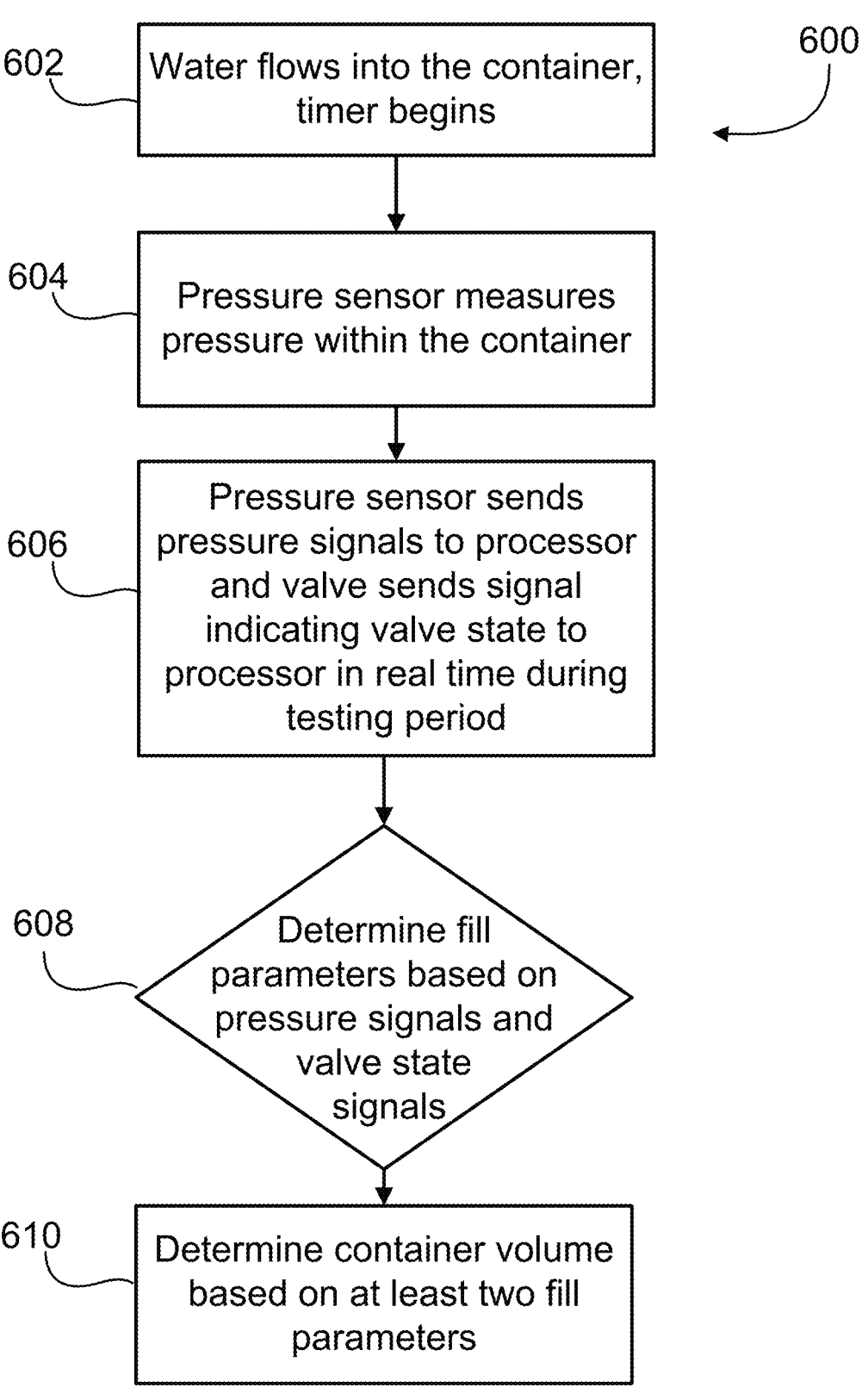

602  Water flows into the container, timer begins

600

604  Pressure sensor measures pressure within the container

606  Pressure sensor sends pressure signals to processor and valve sends signal indicating valve state to processor in real time during testing period 608  Determine fill parameters based on pressure signals and valve state signals 610  Determine container volume based on at least two fill parameters

FIG. 6

| Bibag | Dualysate mEq/L | Flow | # of Fills | Fill Time [s] | Average Initial Fill Delta [s] | Average Baseline Fill Delta [s] | SDEV Baseline Fill Delta [s] | Max delta [s] | Max Delta 2 [s] | $\Delta p/\Delta t$ [mmHd/s] | Min dp/dt (after POI [mmHg/s] | Min dp/dt (End of Delta Max0 [mmHg/s] |
|---|---|---|---|---|---|---|---|---|---|---|---|---|
| 900 | 300 | 26 | 11 | 10.949 | .4079 | 36.416 | 33.448 | 106.214 | N/A | -1.7577 | -34.0425 | 0 |
| 650 | 300 | 26 | 10 | 8.881 | .426 | 33.91 | 6.5728 | 371.098 | N/A | -0.2661 | -12 | 0 |
| 900 | 1000 | 40 | 10 / 5 | 9.944 / 3.849 | .4323 / .907 | 7.940 | 4.1169 | 24.83 | 56.314 | -18.1598 | -29.3296 | -9.4086 |
| 900 | 1000 | 40 | 10 / 6 | 10.212 / 5.021 | .3982 / .762 | 6.067 | 3.261 | 21.347 | 85.872 | -18.0549 | -42.9128 | -16.927 |
| 650 | 1000 | 40 | 9 | 8.883 | .412 | 5.919 | 2.522 | 26.624 | N/A | -7.4809 | -32.8767 | 0 |
| 650 | 1000 | 40 | 10 | 10.058 | .396 | 5.892 | 1.2627 | 32.339 | N/A | -6.3546 | -39.4021 | -4.3478 |

Bicarbonate Setting (mEq/L or mmol/L)

| Dialysate flow QD (mL/min) | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|
| 800 | 300 | 288 | 277 | 267 | 257 | 248 | 240 | 232 | 225 | 218 | 212 | 206 | 200 | 195 | 189 | 185 | 180 |
| 700 | 343 | 329 | 316 | 305 | 294 | 284 | 274 | 265 | 257 | 249 | 242 | 235 | 229 | 222 | 217 | 211 | 206 |
| 600 | 400 | 384 | 369 | 356 | 343 | 331 | 320 | 310 | 300 | 291 | 282 | 274 | 267 | 259 | 253 | 246 | 240 |
| 500 | 480 | 461 | 443 | 427 | 411 | 397 | 384 | 372 | 360 | 349 | 339 | 329 | 320 | 311 | 303 | 295 | 288 |
| 400 | 600 | 576 | 554 | 533 | 514 | 497 | 480 | 465 | 450 | 436 | 424 | 411 | 400 | 389 | 379 | 369 | 360 |
| 300 | 800 | 786 | 738 | 711 | 686 | 662 | 640 | 619 | 600 | 592 | 565 | 549 | 533 | 519 | 505 | 492 | 480 |
| 200 | 1200 | 1152 | 1108 | 1067 | 1029 | 992 | 960 | 929 | 900 | 873 | 847 | 823 | 800 | 778 | 758 | 738 | 720 |

900g — 1402, 1404

Bicarbonate Setting (mEq/L or mmol/L)

| Dialysate flow QD (mL/min) | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|
| 800 | 400 | 384 | 369 | 356 | 343 | 331 | 320 | 310 | 300 | 291 | 282 | 274 | 267 | 259 | 253 | 246 | 240 |
| 700 | 457 | 439 | 422 | 406 | 392 | 378 | 366 | 354 | 343 | 332 | 323 | 313 | 305 | 297 | 289 | 281 | 274 |
| 600 | 533 | 512 | 492 | 474 | 457 | 441 | 427 | 413 | 400 | 388 | 376 | 366 | 356 | 346 | 337 | 328 | 320 |
| 500 | 640 | 614 | 591 | 569 | 549 | 530 | 512 | 495 | 480 | 465 | 452 | 439 | 427 | 415 | 404 | 394 | 384 |
| 400 | 800 | 768 | 738 | 711 | 686 | 662 | 640 | 619 | 600 | 582 | 565 | 549 | 533 | 519 | 505 | 492 | 480 |
| 300 | 1067 | 1024 | 985 | 948 | 914 | 883 | 853 | 826 | 800 | 776 | 753 | 731 | 711 | 692 | 674 | 656 | 640 |
| 200 | 1600 | 1536 | 1477 | 1422 | 1371 | 1324 | 1280 | 1239 | 1200 | 1164 | 1129 | 1097 | 1067 | 1038 | 1011 | 985 | 960 |

DETERMINING A VOLUME OF A
CONTAINER FOR DIALYSIS TREATMENT

TECHNICAL FIELD

This disclosure relates to a dialysis system that is capable of detecting a volume of an attached container and a depletion time for treatment using the detected volume.

BACKGROUND

Dialysis is often prescribed for patients who are unable to clear their blood properly using their renal systems (e.g., kidneys).

The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream across the membrane. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

In an HD treatment, a patient is connected to an extracorporeal blood circuit by inserting a venous bloodline and an arterial bloodline and a dialysis machine takes in the blood from the arterial line, and flows the blood past a semipermeable membrane or filter that is permeable to toxins and fluid. On the other side of the filter, dialysate flows in the opposite direction. The dialysate is a combination of acid, water, and other chemicals, the most notable of which is bicarbonate. The length of treatment time and concentrations of chemicals within the dialysate are prescribed by a physician and are inputted into the dialysis machine prior to beginning dialysis. The prescription includes a concentration of bicarbonate, a dialysate flow rate and if applicable a substitution fluid pump rate, and a treatment length, among other parameters and concentrations. Often the dialysate is mixed using fluids that are previously saturated with a specific substance. For example, bicarbonate solution is created by mixing fluid with powder bicarbonate concentrate. That bicarbonate solution can then be used to mix with other saturated solutions to create dialysate.

In hemofiltration, solutes are removed through the blood primarily through convection resultant of the introduction of substitution into the blood circuit. In hemodiafiltration, the underlying mechanics of both hemodialysis and hemofiltration are used, resulting in diffusive and convective clearance. Substitution fluid can be generated as a bolus, or continuously during treatment at a prescribed rate. The resultant true dialysate consumption rate in hemofiltration and hemodiafiltration treatments are the sum total of the dialysate flow rate and the substitution fluid flow rate.

SUMMARY

In a first aspect, systems and methods include receiving, by a processor of a dialysis machine, a dialysate flow rate, a bicarbonate setting value, a signal from a pressure sensor configured to measure a pressure within a container containing a concentrate as fluid flows from a point upstream of the pressure sensor to the container, and a signal indicating a state of a fill valve upstream of the container as open or closed. The systems and methods include determining, based on the signal received from the pressure sensor and the state of the fill valve during a testing period, fill parameters including: (i) an amount of time elapsed between a completion of an initial fill of the container and an initiation of a first baseline fill of the container during the testing period; (ii) an average of the amounts of time elapsed between each fill valve closing and reopening during baseline fill cycles of the container during the testing period; and (iii) a standard deviation of the amounts of time elapsed between each fill valve closing and reopening during baseline fill cycles of the container during the testing period. The systems and methods include determining a volume of the container based on at least two of the fill parameters. The systems and methods include determining a depletion time in which the concentrate will be depleted from the container based on the volume of the container, the dialysate flow rate, and the bicarbonate setting value. The systems and methods include determining, based on the depletion time, an amount of time remaining before the concentrate will be depleted from the container. The systems and methods include causing the dialysis machine to indicate the amount of time remaining before the concentrate will be depleted from the container to a user.

In some implementations, determining the amount of time elapsed between the completion of the initial fill of the container and the initiation of the first baseline fill of the container includes determining an amount of time elapsed between a time at which the pressure sensor detects that an initial fill completion pressure threshold has been established and a time at which the pressure sensor detects a baseline fill pressure threshold has been established during the testing period.

In some implementations, determining the average of the amounts of time elapsed between each fill valve closing and reopening during baseline fill cycles of the container during the testing period includes determining, based on the signal indicating the state of the fill valve, an average of the amounts of time elapsed between each detection of the state of the fill valve as being closed and subsequently opened after detecting by the pressure sensor that a baseline fill pressure threshold has been established during the testing period.

In some implementations, determining the standard deviation of the amounts of time elapsed between each fill valve closing and reopening during baseline fill cycles of the container during the testing period includes determining, based on the signal indicating the state of the fill valve, a standard deviation of the amounts of time elapsed between each detection of the state of the fill valve as being closed and subsequently opened after detecting by the pressure sensor that a baseline fill pressure threshold has been established during the testing period.

In some implementations, the fill parameters further include an amount of time elapsed during the initial fill of the container where the state of the fill valve is open. In some cases, determining the amount of time elapsed during the initial fill of the container where the state of the fill valve is open includes determining, based on the signal indicating the state of the fill valve, an amount of time elapsed between a time corresponding to an initial flow of fluid from the point upstream of the pressure sensor to the container and a time at which the pressure sensor detects that an initial fill completion pressure threshold has been established.

In some implementations, the fill parameters further include an average of the amounts of time elapsed between each fill valve closing and reopening of a plurality of fill cycles performed during the initial fill of the container. In some cases, determining the average of the amounts of time elapsed between each fill valve closing and reopening of the plurality of fill cycles performed during the initial fill of the container includes determining, based on the signal indicating the state of the fill valve, an average of an amount of time elapsed between each closing of the fill valve and each subsequent opening of the fill valve during the initial fill of the container.

In some implementations, the fill parameters further include a number of fill cycles performed during the initial fill of the container. In some cases, determining the number of fill cycles performed during the initial fill of the container includes determining, based on the signal indicating the state of the fill valve, a number of times the fill valve is opened before an initial fill completion pressure threshold has been established.

In some implementations, the fill parameters further include a rate of change of pressure measured by the pressure sensor between a time at which a pressure threshold of interest is established and a time at which a baseline fill pressure threshold is established.

In some implementations, the fill parameters further include a minimum rate of change of pressure measured by the pressure sensor between a time at which a pressure threshold of interest is established and a time at which a baseline fill pressure threshold is established. In some cases, the pressure threshold of interest is established when a rate of decrease of pressure detected by the pressure sensor exceeds a threshold after an initial fill completion pressure threshold has been established.

In some implementations, the fill parameters further include a rate of change of pressure measured by the pressure sensor during a time period immediately before a baseline fill pressure threshold has been established.

In some implementations, the dialysis machine indicates the depletion time to the user (e.g., via a user interface or a speaker).

In some implementations, determining the volume of the container further include receiving, through a user interface of the dialysis machine, a user confirmation of the volume of the container.

In some implementations, the systems and methods include receiving, by a processor of a dialysis machine, a total treatment time, and a dialysate flow rate including both a dialysate flowrate and substitution fluid pump rate. In some cases, the systems and methods include comparing the depletion time in which the concentrate will be depleted from the container based on the volume of the container, the dialysate flow rate, and the bicarbonate setting value with the total treatment time.

In some implementations, the systems and methods include determining the minimal number of containers required to complete the treatment based on the container volumes supported. In some cases, the systems and methods include causing the dialysis machine to indicate the minimal number of containers with their respective volume required to complete the treatment.

In some implementations, the systems and methods further include adjusting at least one of a temperature of fluid supplied to the container or a pressure within the container to increase utilization of the concentrate.

In some implementations, causing the dialysis machine to indicate the amount of time remaining before the concentrate will be depleted from the container includes causing a display of the dialysis machine to display a visual indicator of the amount of time remaining before the concentrate will be depleted from the container.

In some implementations, the systems and methods further include causing the dialysis machine to generate an auditory and visual notification indicating the amount of time remaining before the concentrate will be depleted from the container to a user. In some cases, causing the dialysis machine to generate an auditory and visual notification includes: determining that the amount of time remaining before the concentrate will be depleted from the container is less than a predetermined amount of time; and in response to determining that the amount of time remaining before the concentrate will be depleted from the container is less than the predetermined amount of time, causing the dialysis machine to generate an auditory and visual notification indicating the amount of time remaining before the concentrate will be depleted from the container to a user. In some cases, the predetermined amount of time is adjustable by the user from 1 to 30 minutes. In some cases, the predetermined amount of time defaults to a time of 20 percent of the depletion time.

In some implementations, the systems and methods further include receiving, by the processor of the dialysis machine, an updated dialysate flow rate, an updated bicarbonate setting, or an updated total treatment time. In response, the systems and methods include determining an updated depletion time in which the concentrate will be depleted from the container based on the volume of the container, determining an updated amount of time remaining before the concentrate will be depleted from the container based on the volume of the container and the updated depletion time, determining the minimal number of containers required to complete the treatment based on the container volumes supported, and determining an amount of time remaining in the treatment.

In some implementations, the systems and methods further include causing the dialysis machine to indicate the updated depletion time to the user.

In some implementations, the systems and methods further include causing the dialysis machine to indicate the updated total treatment time to the user.

In some implementations, the systems and methods further include causing the dialysis machine to indicate the updated remaining treatment time to the user.

In some implementations, the systems and methods further include causing the dialysis machine to indicate the updated amount of time remaining before the concentrate will be depleted from the container to a user.

In some implementations, the systems and methods further include causing the dialysis machine to indicate, if applicable, the updated minimal number of containers with their respective volume required to complete the treatment.

In some implementations, the systems and methods further include generating an auditory notification and/or a visual notification if the minimal number of containers required to complete the treatment has changed or if the size of one or more of the recommended containers required to complete the treatment has changed based on the container volumes supported.

In some implementations, the systems and methods further include receiving, by the processor of the dialysis machine, the detection of a newly installed container. In some cases, the systems and methods include determining, based on the signal received from the pressure sensor and the state of the fill valve during a new testing period, fill parameters including: (i) an amount of time elapsed between a completion of an initial fill of the newly installed container and an initiation of a first baseline fill of the newly installed container during the testing period; (ii) an average of the amounts of time elapsed between each fill valve closing and reopening during baseline fill cycles of the newly installed container during the testing period; and (iii) a standard deviation of the amounts of time elapsed between each fill valve closing and reopening during baseline fill cycles of the newly installed container during the testing period.

In some implementations, the systems and methods include determining a volume of the new container based on at least two of the fill parameters. In some cases, the systems and methods include determining a depletion time in which the concentrate will be depleted from the new container based on the volume of the container, the dialysate flow rate, and the bicarbonate setting value. In some cases, the systems and methods include causing the dialysis machine to indicate the depletion time of the newly installed container to the user. In some cases, the systems and methods include determining, based on the depletion time of the newly installed container, an amount of time remaining before the concentrate will be depleted from the newly installed container. In some cases, the systems and methods include causing the dialysis machine to indicate the amount of time remaining before the concentrate will be depleted from the newly installed container to a user. In some cases, the systems and methods include determining the utilization percentage of the previous container based on the depletion time of the previous container and the remaining time before the concentrate would have been depleted from the previous container.

In some implementations, the systems and methods include determining the new minimal number of containers required to complete the treatment based on the container volumes supported, the depletion time of the newly installed container, the depletion time and the utilization percentage of the previously installed container(s), and the total treatment time. In some cases, the systems and methods include causing the dialysis machine to indicate the new minimal number of containers with their respective volume required to complete the treatment and the utilization percentage of the previously installed container(s). In some cases, the systems and methods include generating an auditory notification and/or a visual notification if the minimal number of containers required to complete the treatment has changed or if the size of one or more recommended containers required to complete the treatment has changed based on the container volumes supported.

In some implementations, the initial fill is triggered when the pressure sensor detects that the pressure within the container is below an initial fill trigger pressure threshold.

In some implementations, the initial fill is completed when the pressure sensor detects that the pressure within the container corresponds to an initial fill completion pressure threshold and is maintained for a predetermined amount of time.

In some implementations, the baseline fill is triggered when the pressure sensor detects that the pressure within the container is below a baseline fill pressure threshold after the initial fill is completed.

In some implementations, the initial fill trigger pressure threshold being lower than the baseline fill pressure threshold and the baseline fill pressure threshold being lower than the initial fill completion pressure threshold. In some cases, the initial fill trigger pressure threshold is 70 mmHg, the baseline fill pressure threshold is 90 mmHg, and the initial fill completion pressure threshold is 150 mmHg.

In some implementations, the fill parameters further include detection of a second initial fill of the container during the testing period. In some cases, detecting the second initial fill of the container during the testing period includes determining, based on signals received from the pressure sensor, that the initial fill trigger pressure threshold has been established after the initial fill completion pressure threshold has been established during the testing period.

In some implementations, determining the volume of the container based on at least two of the fill parameters includes comparing each of the at least two of the fill parameters to a corresponding threshold for a particular container volume. In some cases, determining the volume of the container based on at least two of the fill parameters includes calculating a weighted average based on the comparison of each of the at least two of the fill parameters to the corresponding threshold.

In a second aspect, a system includes a container containing bicarbonate and is configured to receive RO water and deliver bicarbonate solution at a prescribed rate. The system includes a dialysis machine including a pressure sensor configured to detect fluid pressure within the container. The dialysis machine includes a dialysate fluid circuit configured to deliver dialysate at a prescribed dialysate flow rate. The dialysis machine includes a fill valve configured to open and close to control a flow of the RO water into the container. The dialysis machine includes a data processing apparatus configured to receive signals from the pressure sensor, a signal indicating the prescribed dialysate flow rate, a signal indicating a prescribed bicarbonate setting, and a signal indicating a state of the fill valve as open or closed.

In some implementations, the data processing apparatus is configured to, based on the signals received from the pressure sensor and the signals indicating the state of the fill valve, determine fill parameters including: (i) an amount of time elapsed between a completion of an initial fill of the container and an initiation of a first baseline fill of the container during a testing period, (ii) an average of the amounts of time elapsed between each fill valve closing and reopening during baseline fill cycles of the container during the testing period, and (iii) a standard deviation of the amounts of time elapsed between each fill valve closing and reopening during baseline fill cycles of the container during the testing period.

In some implementations, the data processing apparatus is configured to determine a volume of the container based on at least two of the fill parameters. The data processing apparatus is configured to determine a depletion time in which the bicarbonate will be depleted from the container based on the volume of the container, the prescribed dialysate flow rate, and the prescribed bicarbonate setting. The data processing apparatus is configured to determine, based on the depletion time, an amount of time remaining before the bicarbonate will be depleted from the container. The data processing apparatus is configured to cause the dialysis machine indicate the amount of time remaining before the bicarbonate will be depleted from the container to a user.

In some implementations, the system further includes a fluid line coupled to the container containing the bicarbonate, the fluid line being configured to deliver the RO water to the container via a fill valve for mixing with a portion of the bicarbonate to produce a solution of bicarbonate.

In some implementations, the system further includes a user interface configured to prompt a user to input a prescription including the prescribed dialysate flow rate and the prescribed bicarbonate setting.

In some implementations, the data processing apparatus is configured to notify the user when the amount of time remaining before the bicarbonate will be depleted from the container is less than a predetermined amount of time.

In some implementations, the data processing apparatus is configured to cause the dialysis machine to perform the initial fill when the pressure sensor detects that the fluid pressure within the container is below an initial fill trigger pressure threshold.

In some implementations, the data processing apparatus is configured to cause the dialysis machine to complete the initial fill when the pressure sensor detects the pressure within the container meets an initial fill completion pressure threshold.

In some implementations, the data processing apparatus is configured to cause the dialysis machine to perform the baseline fill when the pressure sensor detects that the fluid pressure within the container is below a baseline fill pressure threshold after the completion on the initial fill, the initial fill trigger pressure threshold being lower than the baseline fill pressure threshold and the baseline fill pressure threshold being lower than the initial fill completion pressure threshold. In some cases, the initial fill trigger pressure threshold is 70 mmHg, the baseline fill pressure threshold is 90 mmHg, and the initial fill completion pressure threshold is 150 mmHg.

In some implementations, the fill parameters further include an amount of time elapsed during the initial fill of the container where the state of the fill valve is open.

In some implementations, the fill parameters further include an average of the amounts of time elapsed between each fill valve closing and reopening during a plurality of fill cycles performed during the initial fill of the container.

In some implementations, the fill parameters further include a number of fill cycles performed during the initial fill of the container.

In some implementations, the predetermined amount of time is adjustable from 1 to 30 minutes.

In some implementations, the predetermined amount of time defaults to a time of 20 percent of the depletion time.

In some implementations, the fill parameters further include a rate of change of pressure measured by the pressure sensor between a time at which a pressure threshold of interest is established an initial fill completion pressure threshold being established and a time at which a baseline fill pressure threshold is established.

In some implementations, the fill parameters include a rate of change of pressure measured by the pressure sensor during a time period immediately before a baseline fill pressure threshold has been established.

In some implementations, the fill parameters include a minimum rate of change of pressure measured by the pressure sensor between a time at which a pressure threshold of interest is established and a time at which a baseline fill pressure threshold is established. In some cases, the pressure threshold of interest is established when a rate of decrease of pressure detected by the pressure sensor exceeds a threshold after an initial fill completion pressure threshold has been established.

In some implementations, the system further includes a dialysate fluid circuit configured to deliver substitution fluid at a prescribed substitution fluid rate. In some cases, the system further includes a fluid line coupled to a substitution fluid pump, the fluid line configured to deliver the substitution fluid. In some cases, the data processing apparatus is further configured to receive signals of a total treatment time, and a dialysate flow rate including both a dialysate flowrate and substitution fluid pump rate. In some cases, the data processing apparatus is further configured to compare the depletion time in which the concentrate will be depleted from the container based on the volume of the container, the dialysate flow rate, and the bicarbonate setting value with a total treatment time. In some cases, the data processing apparatus is further configured to determine the minimal number of containers required to complete the treatment based on the container volumes supported. In some case, the data processing apparatus is further configured to cases the dialysis machine to indicate the minimal number of containers with their respective volume required to complete the treatment.

In some implementations, the system includes receiving, by the processor of the dialysis machine, an updated dialysate flow rate, an updated bicarbonate setting, or an updated total treatment time. In response, the system is configured to: (i) determine an updated depletion time in which the concentrate will be depleted from the container based on the volume of the container, (ii) determine an updated amount of time remaining before the concentrate will be depleted from the container based on the volume of the container and the updated depletion time, (iii) determine the minimal number of containers required to complete the treatment based on the container volumes supported, and (iv) determine an amount of time remaining in the treatment.

In some implementations, the system is configured to cause the dialysis machine to indicate the updated depletion time to the user.

In some implementations, the system is configured to cause the dialysis machine to indicate the updated total treatment time to the user.

In some implementations, the system is configured to cause the dialysis machine to indicate the updated remaining treatment time to the user.

In some implementations, the system is configured to cause the dialysis machine to indicate the updated amount of time remaining before the concentrate will be depleted from the container to a user.

In some implementations, the system is configured to cause the dialysis machine to indicate, if applicable, the updated minimal number of containers with their respective volume required to complete the treatment.

In some implementations, the system is configured to generate an auditory notification and/or a visual notification if the minimal number of containers required to complete the treatment has changed or if the size of one or more of the recommended containers required to complete the treatment has changed based on the container volumes supported.

In some implementations, the system is further configured to receive, by the processor of the dialysis machine, the detection of a newly installed container. In some cases, the system is further configured to determine, based on the signal received from the pressure sensor and the state of the fill valve during a new testing period, fill parameters including: (i) an amount of time elapsed between a completion of an initial fill of the newly installed container and an initiation of a first baseline fill of the newly installed container during the testing period, (ii) an average of the amounts of time elapsed between each fill valve closing and reopening during baseline fill cycles of the newly installed container during the testing period, and (iii) a standard deviation of the amounts of time elapsed between each fill valve closing and reopening during baseline fill cycles of the newly installed container during the testing period.

In some implementations, the system is further configured to determine a volume of the new container based on at least two of the fill parameters.

In some implementations, the system is further configured to determine a depletion time in which the concentrate will be depleted from the new container based on the volume of the container, the dialysate flow rate, and the bicarbonate setting value.

In some implementations, the system is further configured to cause the dialysis machine to indicate the depletion time of the newly installed container to the user.

In some implementations, the system is further configured to determine, based on the depletion time of the newly installed container, an amount of time remaining before the concentrate will be depleted from the newly installed container.

In some implementations, the system is further configured to cause the dialysis machine to indicate the amount of time remaining before the concentrate will be depleted from the newly installed container to a user.

In some implementations, the system is further configured to determine the utilization percentage of the previous container based on the depletion time of the previous container and the remaining time before the concentrate would have been depleted from the previous container.

In some implementations, the system is further configured to determine the new minimal number of containers required to complete the treatment based on the container volumes supported, the depletion time of the newly installed container, the depletion time and the utilization percentage of the previously installed container(s), and the total treatment time.

In some implementations, the system is further configured to cause the dialysis machine to indicate the new minimal number of containers with their respective volume required to complete the treatment and the utilization percentage of the previously installed container(s).

In some implementations, the system is further configured to generate an auditory notification and/or a visual notification if the minimal number of containers required to complete the treatment has changed or if the size of one or more recommended containers required to complete the treatment has changed based on the container volumes supported.

In some implementations, the system is further configured to log the number of bags used, their respective sizes, and their respective utilization percentages.

Implementations can include one or more of the following advantages.

In some implementations, by automatically determining the volume of a container coupled to the hemodialysis machine, the systems and methods of the present disclosure enable more efficient preparation of the hemodialysis machine for treatment by eliminating the need for the user to manually input or scan the container size. Instead, the systems and methods of the present disclosure streamline the input of the container volume and prompt the operator to affirm an automatically determined container size rather than enter the container volume in manually.

In some implementations, by calculating and alerting an operator of the estimated depletion time (e.g., the amount of time remaining before a container will be depleted), the systems and methods of the present disclosure enable more efficient scheduling of clinic employees by providing advanced knowledge of when the container will need to be replaced.

In some implementations, by providing real-time adjustments of the estimated depletion time and estimated remaining time before the container is depleted, an accurate estimate of when the container will be depleted is maintained after adjustments to the dialysate flow rate, the substitution fluid pump rate, and the bicarbonate setting. In some examples, this is advantageous as the dialysate flow rate is not only adjustable during treatment by the user, but can also be automatically adjusted by the dialysis machine during routines such as pressure holding tests (which ensure proper machine hydraulic function), or resultant of an automated dialysate flow rate (which is set as a scaled value of the blood flow rate), thereby making manual assessment of the estimated depletion time impractical in some cases. Likewise, the substitution fluid pump starts, stops, and is adjusted for various reasons during hemofiltration and hemodiafiltration treatments making a manual assessment of the estimated depletion time impractical.

Moreover, through knowledge of the estimated depletion time and total treatment time, the systems and methods provide the operator with an estimate of the total number of containers needed to complete the treatment. In some examples, the systems and methods provide a recommendation (e.g., an optimal recommendation) of the size of subsequently used containers to reduce (e.g., minimize) the number of containers used. In some examples, this reduces waste and cost.

In some embodiments, this recommendation can be dynamic, where changes to the estimated depletion time, for example resultant of an adjustment of the dialysate flow rate or substitution fluid pump rate, will result in potential modifications to the estimated total number of containers needed and the recommended size of subsequently used containers. In the case of a modification to the optimal recommendation of containers in sizes, the operator would be notified providing streamlining of the clinician workflow.

In some embodiments, the number of containers used, their respective utilization percentage, and their respective volume are logged by the machine and are capable of being viewed and uploaded from the machine. This provides the advantage, particularly in the home environment, of the ability to obtain a better understanding of the weekly or monthly utilization of containers to allow for better planning of ordering the appropriate size and number of containers. In a clinical setting, this provides the further benefit of allowing review of utilization history to identify frequent underutilization which may point to the need for additional training and/or adjustment of the container sized used during the day to minimize waste and cost.

The details of one or more embodiments are set forth in the accompanying drawings and the description below. Other aspects, features, and advantages of the disclosure will be apparent from the description and drawings, and from the claims.

DESCRIPTION OF DRAWINGS

FIG. 2 depicts a container configured to be connected to the dialysis machine of the dialysis system of FIG. 1.

FIG. 6 depicts a process for determining a volume of a container coupled to a dialysis machine.

FIG. 14 depicts a table of depletion times for particular container volumes at various dialysate flow rates and bicarbonate concentrations.

DETAILED DESCRIPTION

Figure 1:
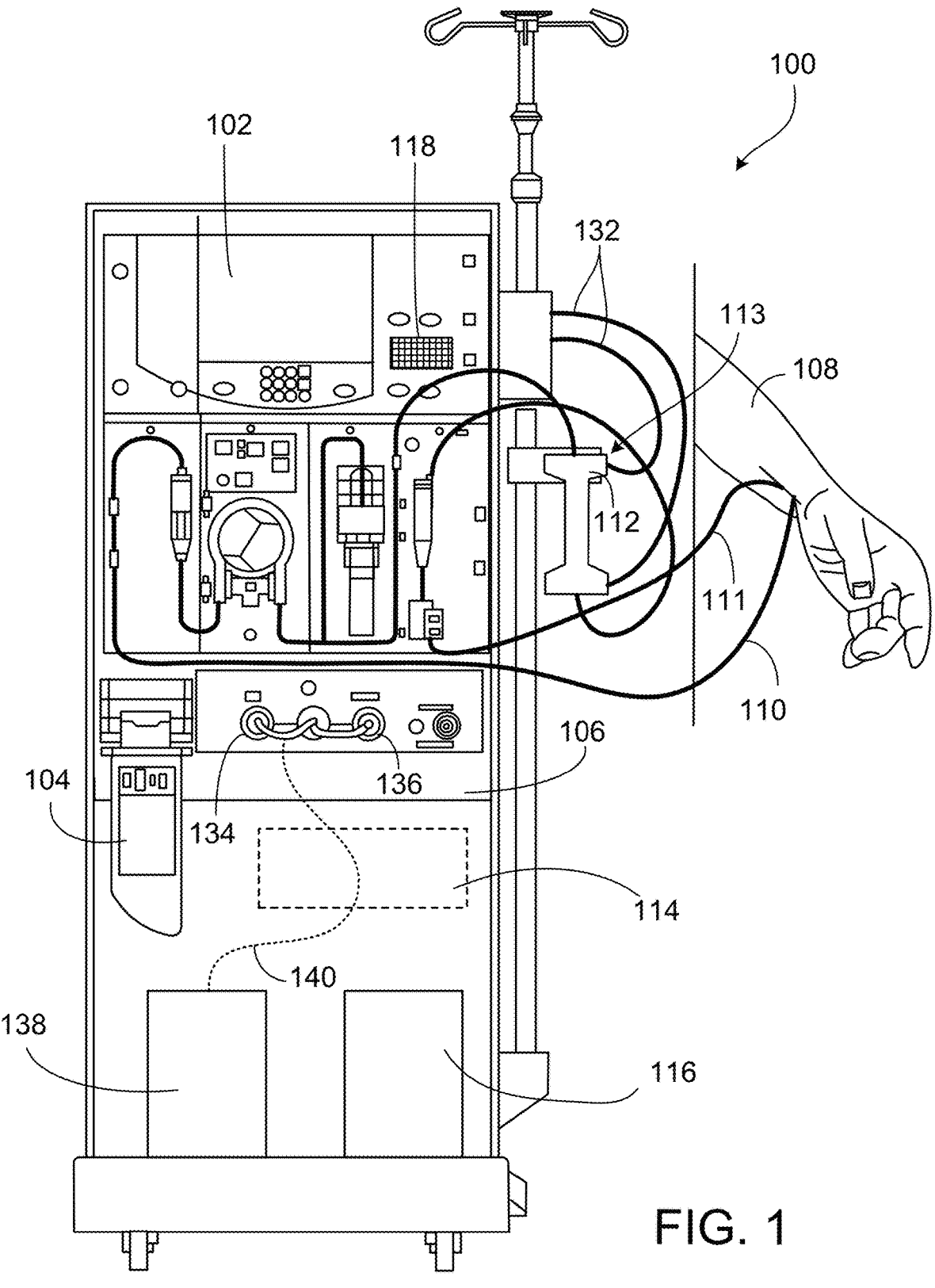
FIG. 1 depicts a dialysis system during a dialysis treatment.

Referring to FIG. 1, a hemodialysis system 100 includes a hemodialysis machine 106 to which a disposable blood component set 113 that forms a blood circuit is connected. The hemodialysis machine 106 includes a processor 114 and a user interface 102 that can be used to control the hemodialysis machine 106. For example, the user interface 102 can be used to adjust an Acid/Bicarb alert (which is explained in further detail below). The hemodialysis system 100 also includes a dialyzer 112, a container 104 connected the hemodialysis machine 106, and a fluid source 116 that is fluidly connected to the container 104.

Further details regarding the machines described throughout this disclosure can be found in U.S. application Ser. No. 16/012,945 which issued as U.S. Pat. No. 11,123,464, the contents of which are hereby incorporated by reference in entirety.

Figure 4:
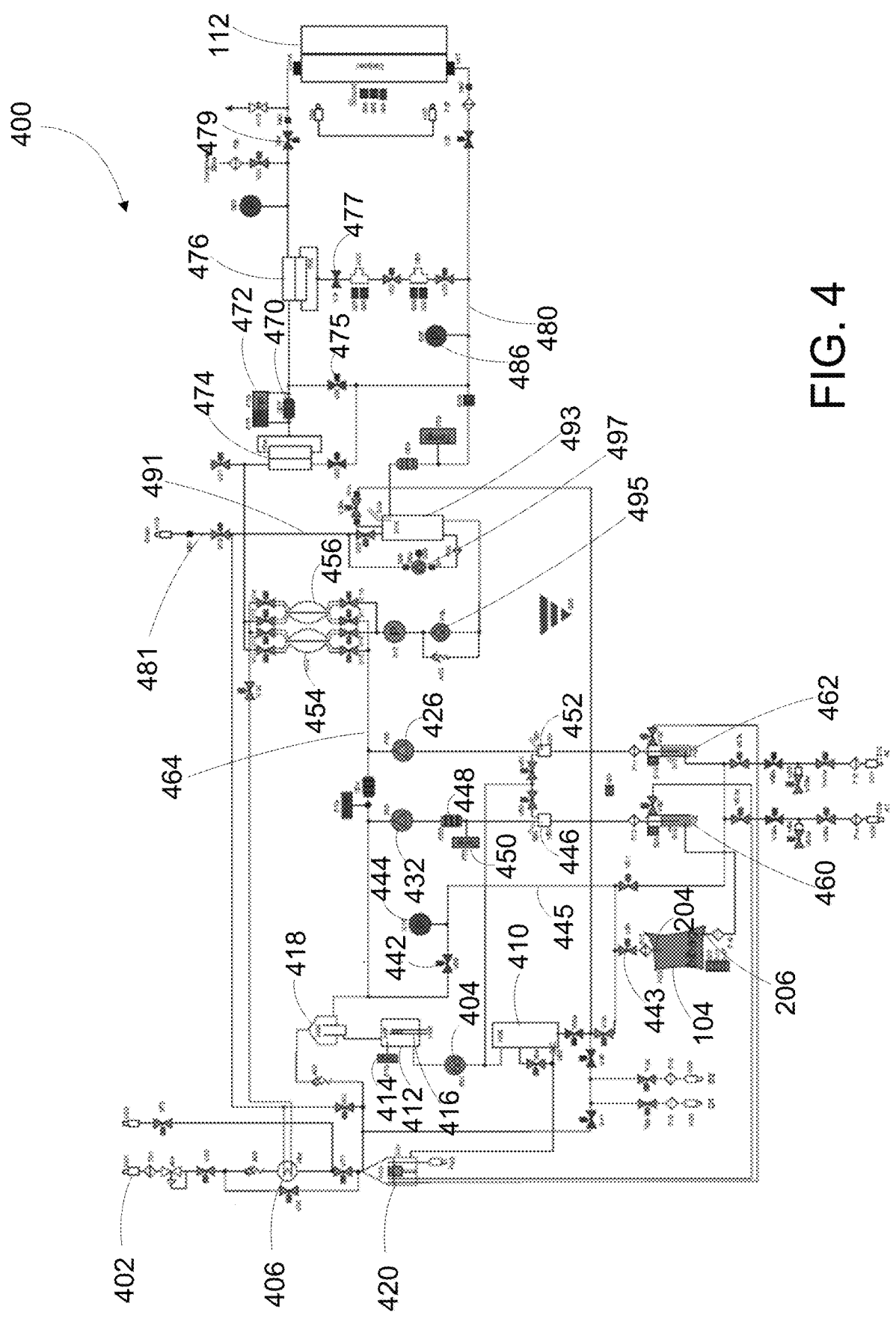
FIG. 4 is a schematic of a dialysate circuit of the dialysis system of FIG. 1.

During hemodialysis treatment, arterial patient line 110 and venous patient line 111 are connected to a patient 108 and blood is circulated through the blood lines 110, 111 and components of the blood component set 113, including the dialyzer 112. At the same time, dialysate is circulated through a dialysate circuit to the dialyzer 112 via fresh and spent dialysate lines 132 connected to the hemodialysis machine 106 and various other dialysate components (as shown in FIG. 4).

The dialysate passes through the dialyzer 112 simultaneously with the blood. The blood and dialysate passing through the dialyzer 112 are separated from one another by a semi-permeable structure (e.g., a semi-permeable membrane) of the dialyzer 112. As a result of this arrangement, toxins are removed from the patient's blood and collected in the dialysate. The filtered blood exits the dialyzer 112 is returned to the patient 108 via the venous line 111. The dialysate that exits the dialyzer 112 via the spent dialysate line 132 includes toxins removed from the blood and is commonly referred to as "spent dialysate." The spent dialysate is routed from the dialyzer 112 to a drain via a drain line.

The fresh dialysate flowing through the dialysate circuit during treatment is produced by mixing powdered bicarbonate contained within the container 104 with additional fluid and substances. The hemodialysis machine 106 is also capable of being supplied liquid bicarbonate through a bicarbonate connector 134. The hemodialysis machine 106 is also capable of being supplied acid concentrate using a liquid source via an acid connector 136. The connectors 134, 136 allow respective tubes (e.g., wands) to be placed in concentrate containers 138. While only one concentrate container 138 is shown in FIG. 1, more than one can be used with the hemodialysis machines described herein.

In some examples, the concentrate containers 138 are one gallon jugs. In some examples, in-lieu of concentrate containers 138 the same liquid from a central delivery source is used in a blood treatment. In some examples, bicarbonate connector 134 is not used (e.g., if a dried source is not used during a blood treatment).

As will be described in further detail herein, the volume of the container 104 connected to the hemodialysis machine 106 can be determined by the processor 114 based on one or more signals received from a pressure sensor upstream of the container 104 and signals indicating the state of a valve controlling the flow of fluid into the container 104 from the fluid source 116. The volume of the bicarbonate container 104 is used by the processor 114 to determine the duration of time which the container 104 can supply saturated bicarbonate solution to achieve a prescribed bicarbonate setting (e.g., concentration) at a particular dialysate machine flow rate.

Some machines are capable of generating substitution fluid through use of a substitution fluid pump. Substitution fluid, or substituate, is dialysate that has been further filtered through use of a second filtered for administration into the blood circuit via the arterial and/or the venous patient line. This substitution fluid can be used in-lieu of saline for the purpose of priming the extracorporeal circuit, and additionally allows for alternative dialysis treatment modalities such as hemofiltration and hemodiafiltration. Additionally, the blood reinfusion process performed at the end of treatment can leverage the substitution fluid to return the blood without the need for saline.

In the case of dialysis machines equipped with a substitution fluid pump, the volume of the bicarbonate container 104 is used by the processor 114 to determine the duration of time which the container 104 can supply saturated bicarbonate solution to achieve a prescribed bicarbonate concentration at a particular dialysate flow rate and substitution fluid flow rate. Further details regarding these flowrates are described with reference to FIG. 14 below.

The bicarbonate solution concentration, the dialysate flow rate, and if applicable, the substitution fluid pump rate to be used during treatment are prescribed by a medical professional, and are received by the processor 114 of the hemodialysis machine 106 (e.g., by inputting the prescription using the user interface 102 of the hemodialysis machine 106 or through insertion of a patient specific card). In some implementations, the user interface 102 of the hemodialysis machine can include controls to allow an operator of the hemodialysis machine 106 to input prescription information for the dialysis treatment, such as the dialysate solution concentrations and the dialysate flow. In some implementations, the prescription information is loaded off of a patient specific card inserted into the hemodialysis machine 106 and is confirmed through the user interface 102. In some implementations, the prescription information for controlling the dialysis treatment is received wirelessly by the processor 114 of the hemodialysis machine 106 from a remote computing device, such as a computing device associated with a medical professional. The prescription information and the volume of the container 104 can be used by the processor 114 to automatically determine an amount of time remaining before the bicarbonate within the container 104 will be depleted.

Figure 3:
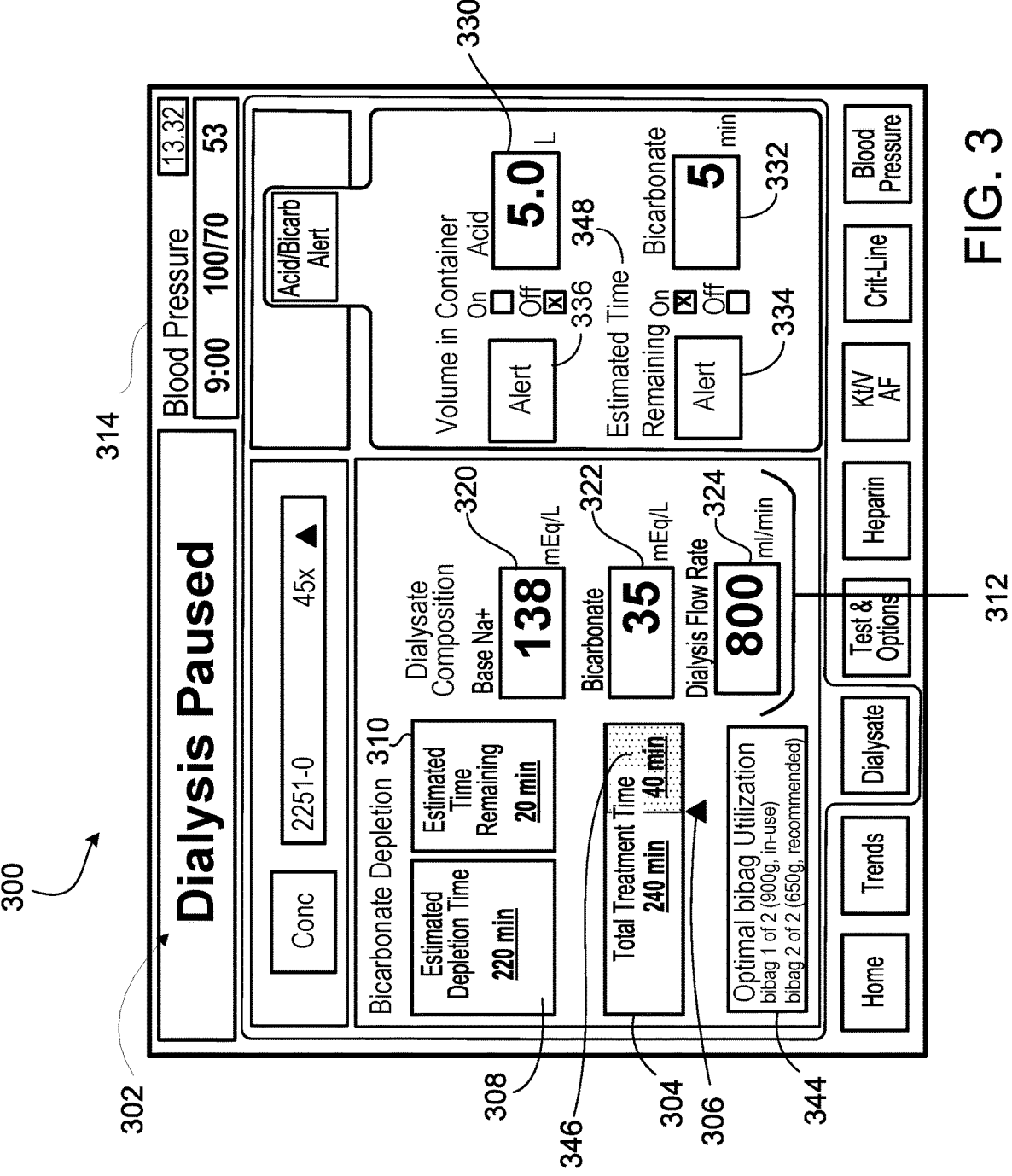
FIG. 3 depicts a user interface of the dialysis system of FIG. 1 displaying, among other things, a calculated depletion time.

FIG. 3 illustrates an example user interface 300 of the hemodialysis machine 106. The user interface 300 is an example of the user interface 102 shown in FIG. 1. The user interface 300 is configured to display information related to the hemodialysis treatment and enable an operator of the hemodialysis machine 106 to input information related to the patient and the treatment to be carried out by the hemodialysis machine 106.

For example, the user interface 300 can display information related to the patient 108, such as the current blood pressure 314 of the patient. The user interface 300 also displays prescription information 312 that is used by the processor 114 to carry out the hemodialysis treatment. The prescription information 312 can include a prescribed sodium concentration 320, a prescribed bicarbonate concentration 322, a prescribed dialysate flow rate 324, and if applicable, a prescribed substitution fluid pump rate.

The user interface 300 also displays the estimated depletion time 308 for the container 104 attached to the hemodialysis machine 106 and the estimated amount of time remaining 310 before the bicarbonate within the container 104 will be depleted. As will be described in further detail herein, the estimated depletion time 308 and the estimated amount of time remaining 310 before the bicarbonate within the container 104 will be depleted are automatically determined and dynamically updated by the processor 114 of the hemodialysis machine 106 based on the volume of the container 104 and the prescription information 312.

The user interface 300 includes an indicator of the treatment time 304, remaining treatment time 346, and an estimated/recommended number of bicarbonate containers for treatment completion (344) which are determined by the processor 114 of the hemodialysis machine 106 based on prescription information provided to the hemodialysis machine 106. In some examples, the indicator is a pop-up that appears on the user interface 300. In such examples, the pop-up provides a confirmation of the volumes, and the acid/bicarb alert refers to liquid volumes not dried powder volumes.

In some examples, the user interface 300 displays the total treatment time, the remaining treatment time (e.g., via display 346), and the total number of estimated bicarb containers required (e.g., via display 344). Displaying the remaining treatment time is beneficial because it lets the medical professionals visually compare to estimated time remaining to see if they will need another bicarb container before the treatment finishes. Displaying of the total estimated bicarb containers required could be optimized based on the real-time average of the dialysate and substitution fluid rate up to the current point in the treatment with consideration of any expected (or manually adjusted dialysate flowrate, substitution flowrate, or bicarb mEq/L setting).

For example, the hemodialysis machine 106 could display an optimal bibag utilization such as "bibag 1 of 2 (900 g, in-use)" and "bibag 2 of 2 (650 g, recommended)." In this example, displaying the optimal bibag utilization allows the medical professions to prepare for container adjustment during the 240 minute treatment (e.g., assuming the 900 g bibag generates an estimated depletion time of 220, a second 650 g bibag would be required to support the remaining 20 or more minutes of treatment after removal of the depleted 900 g bibag).

Using the values shown in FIG. 3, let's consider the following hypothetical. The current bag springs a leak when 30 minutes of treatment remain and the medical professional replaces the leaking bag with a new bibag, and then processor determines it's a 650 g bibag. In this case, the hemodialysis machine 106 would update the display to show the optimal bibag utilization as "bibag 1 of 2 (900 g, 95% depleted)", as the 900 g bibag provided bicarbonate for 210 of the estimated 220 potential minutes before expected depletion, and "bibag 2 of 2 (650 g, in-use)." In some examples, when the substitution fluid pump is turned off or its rate is adjusted, this would also change the estimated depletion time, the estimated remaining time, and could also result in a new bag recommendation (e.g., bibag 2 of 2 no longer being required). In general, the hemodialysis machine 106 continuously updates the recommendation and notifies the medical professional when the optimal recommendation changes.

As can be seen in FIG. 3, an arrow illustrates the position of a progress bar 306 indicative of the amount of the total treatment time that has elapsed. The user interface 300 may display the graphical treatment time indicator 304 with progress bar 306, or may alternatively display a text-only indicator of total treatment time, remaining treatment time, and/or duration of treatment. The estimated depletion time 308 and estimated remaining time 310 are updated by the processor 114 throughout treatment based on changes to the prescription such as bicarbonate setting or treatment time, and additionally based on machine parameter changes to the dialysate flow rate and/or substitution fluid pump. The progress bar 306 and estimated time remaining 310 can also be updated based on changes to the treatment time, or delays in treatment that can result from machine alarms that resultant and bypass of dialysate from the dialysate circuit to the dialyzer.

The user interface 300 also includes a bicarbonate alert toggle button 334 and acid alert toggle button 336 that can be used by an operator of the hemodialysis machine 106 to select whether the hemodialysis machine 106 provides an alert when either the bicarbonate source or an acid concentrate source will be depleted.

Figure 7:
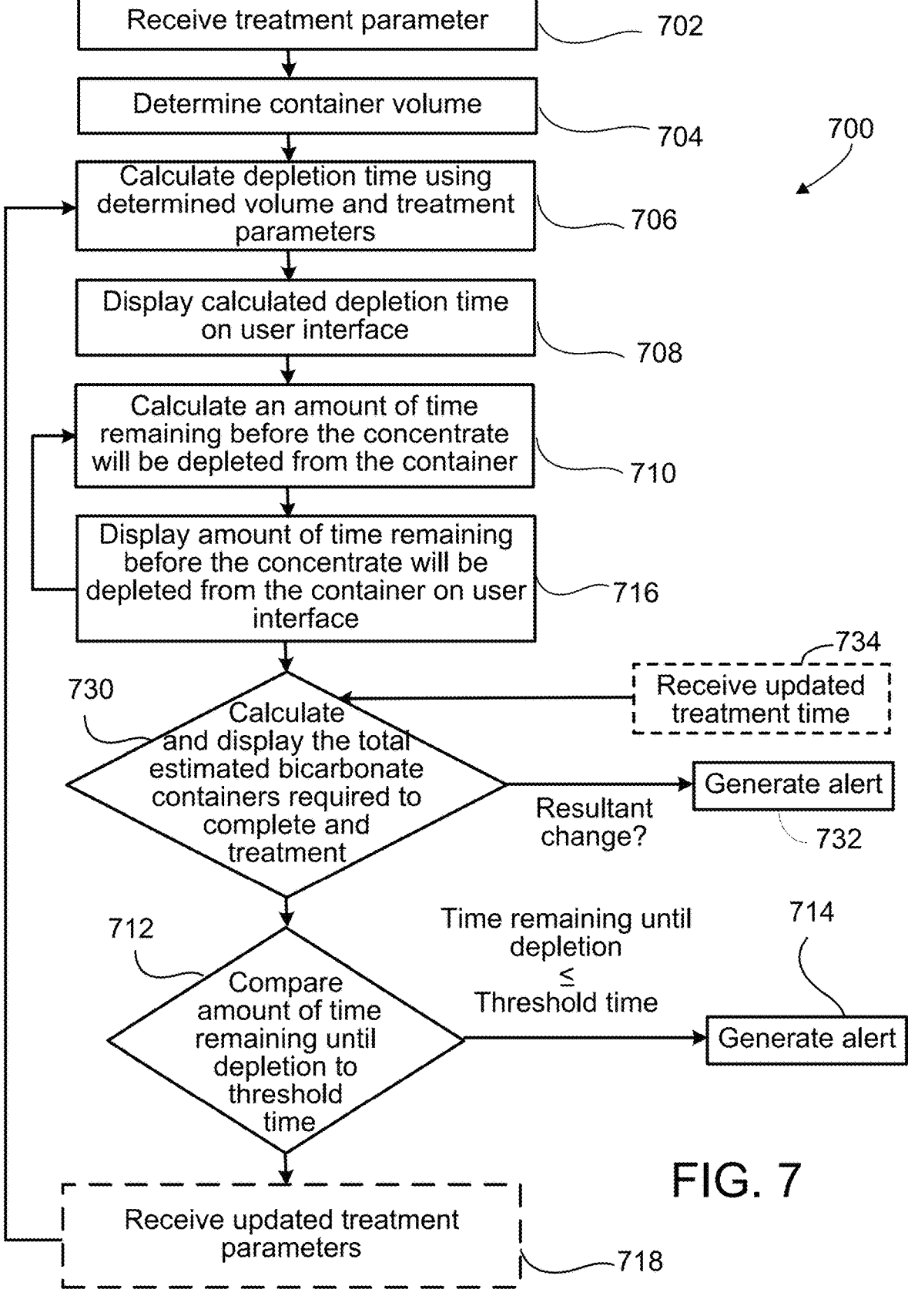
FIG. 7 depicts a process performed by a dialysis machine to calculate a depletion time of a container coupled to the dialysis machine.

As shown in FIG. 7, steps 712 and 714 illustrate that the alert of the hemodialysis machine 106 can be based on a time threshold that is based on an estimate time remaining threshold 332. In some examples, the processor 114 displays "min" on the right-hand side of the Bicarbonate alert display 332 as shown in FIG. 3. For example, as shown in FIG. 1, the hemodialysis machine 106 can include a bicarbonate wand connected to the bicarbonate connector 134. When the bicarbonate wand is not used, the hemodialysis machine 106 determines that a bibag (dried bicarbonate source) should be connected to the hemodialysis machine 106. As a result, this bicarb alert button automatically changes from an "L" to a "min" when the machine detects a dried source as a unit of volume for an alert is not applicable for a dried bicarbonate source where liquid bicarbonate is being generated by the hemodialysis machine 106.

In some examples, this functionality is reserved for liquid acid and bicarbonate sources where a known container volume is entered by the user and the machine would generate an alarm when the container volume remaining reached 20%. As can be seen in FIG. 3, the units for an Acid alert 330 are "L" or liters, and the units for a Bicarbonate alert 332 are in "min" or minutes. Additionally, the Acid alert header text is "Volume in Container" and the Bicarbonate alert header text 348 is "Estimated Time Remaining". The hemodialysis machine 106 is capable of determining the source of bicarbonate based on the state of the door that holds the bicarbonate container in addition to the state of the bicarbonate connector that can be connected to a liquid bicarbonate source, and accordingly will toggle the units for the Bicarbonate alert 332 from "L" to "min" and the bicarbonate alert header text 348 from "Volume in Container" to "Estimated Time Remaining" based on the detected bicarbonate source. An operator can use bicarbonate alert toggle button 334 to turn on or off the bicarbonate alert feature, and in response to the processor 114 determining that the estimated depletion time 308, can provide a default value for the Bicarbonate Alert 332 equal to 20% of estimated depletion time 308. When the processor 114 determines that the estimated time remaining 310 equals the Bicarbonate Alert 332 value, the processor 114 causes the hemodialysis machine 106 to generate an alert. In some implementations, the alert generated by the hemodialysis machine 106 is a visual alert indicating the estimated time remaining before depletion is below a threshold (e.g., "bibag life low" can be displayed on the user interface). In some implementations, the alert generated by the hemodialysis machine 106 is additionally an auditory alert emitted by a speaker 118 of the hemodialysis machine 106 indicating the estimated time remaining before depletion is below a threshold.

As will be described in further detail herein, the volume of the bicarbonate container 104 can automatically be determined by the processor 114 before beginning treatment based on one or more signals received from a pressure sensor upstream of the container 104 and signals indicating the state of a valve controlling the flow of fluid into the container 104 from the fluid source 116.

Figure 2:
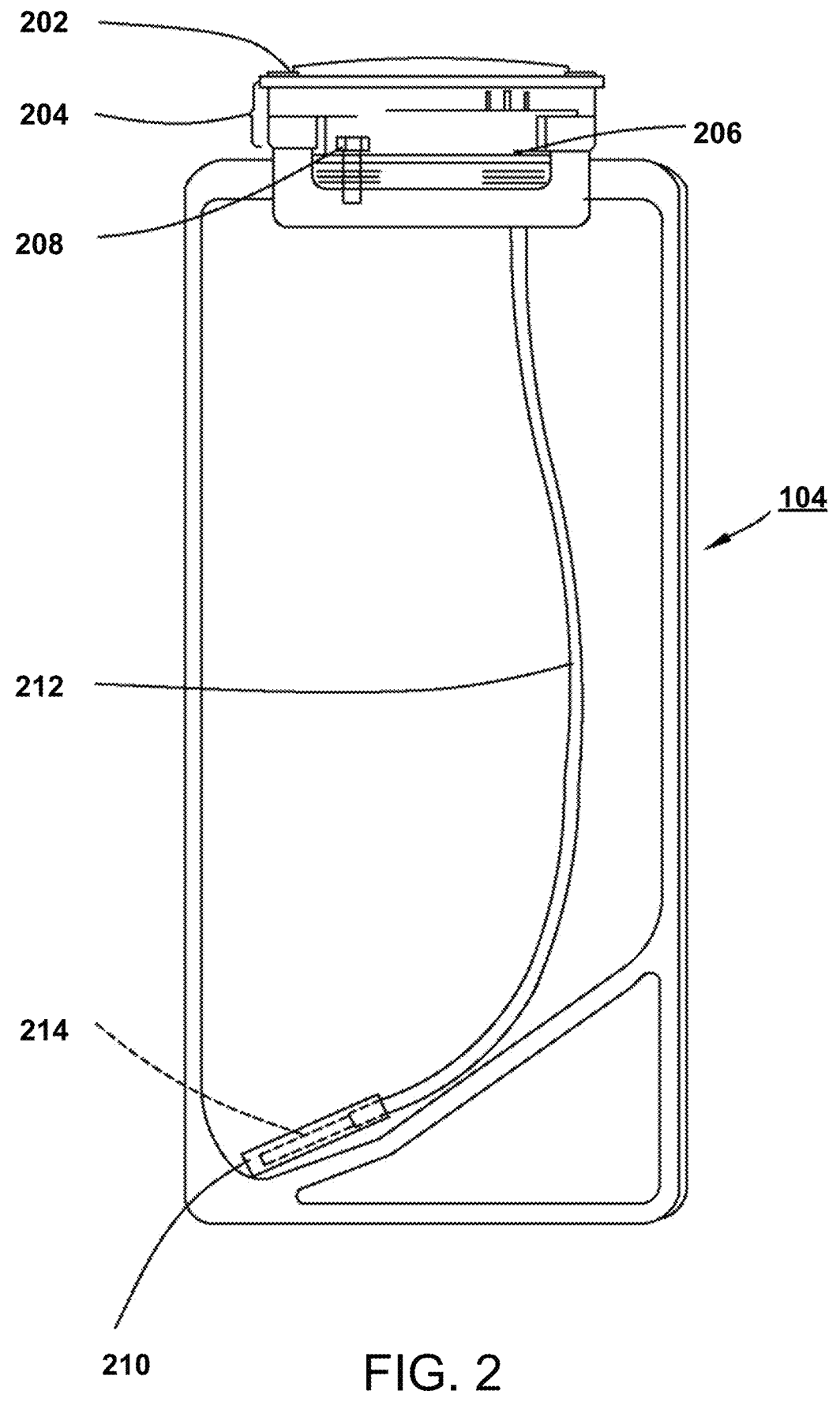

FIG. 2 depicts an example container 104 that is configured to be coupled to the hemodialysis machine 106 for generating bicarbonate solution. The container 104 includes a powdered bicarbonate concentrate that is dissolvable with a fluid to create a bicarbonate solution. For example, the hemodialysis machine 106 is configured to create a bicarbonate solution by flowing water into the container 104 through an inlet 208 that is integrated into a connector 204 of the container 104. The bicarbonate solution can be drawn into the dialysate circuit of the hemodialysis machine 106 through an outlet port 206 of the container 104.

To prepare the hemodialysis machine 106 for treatment, the operator fluidly connects the container 104 to the dialysate circuit of the hemodialysis machine 106 by connecting the connector 204 of the cap 202 to a fluid line of the hemodialysis machine 106. The connector 204 of the container 104 facilitates the fluid connection of the inlet port 208 to the fluid source 116 and facilitates the fluid connection of the outlet port 206 of the container 104 to the dialyzer 112. The connector 204 of the container 104 is universal for every volume of container that can be connected to the hemodialysis machine 106, allowing for uniform connection attachment procedures regardless of the size of the container 104. Different sizes of containers 104 can be attached to the hemodialysis machine 106. For example, the hemodialysis machine 106 may utilize containers having 650 g of bicarbonate powder and containers having 900 g of bicarbonate powder, which each have a different volume.

The container 104 is fluidly coupled to the dialyzer via the outlet 206. As can be seen in FIG. 4, the dialysate circuit 400 includes a bicarbonate pump 432 that is positioned downstream of the container 104 and is operated to pump bicarbonate solution out of the container 104 through the outlet 206 of the container 104 and into the dialysate circuit 400. Bicarbonate solution is withdrawn from the container 104 through an opening 210 of a tube 212 inside the container 104 that is fluidly connected to the outlet 206. The opening 210 of the tube 212 is covered by a filter 214 to ensure only fluid is removed from the container 104. As will be described in further detail herein, the bicarbonate solution withdrawn from the container 104 is combined with an acid concentrate solution within the dialysate circuit to produce dialysate. The dialysate then flows through the dialyzer 112 during treatment to clear the patient's blood of toxins.

FIG. 4 is a schematic showing the flow paths of fluids into, through, and out of the dialysate circuit 400 of the hemodialysis machine 106. The dialysate circuit 400 includes a number of dialysate components that are fluidly connected to one another via a series of fluid lines. A water inlet port 402 is configured to receive water from an external source and provide the water to a heat exchanger 406 via the fluid line. Heat exchanger 406 is configured to warm the water received by the dialysate circuit 400 through the water inlet port 402 using the heat of spent dialysate (or other fluid) flowing on an opposite side of the heat exchanger 406.

After exiting the heat exchanger 406, the warmed water flows to a hydrochamber 420. The hydrochamber 420 may be an example of the fluid source 116 shown in FIG. 1. A degassing pump 404 can be operated to draw the warmed water from the hydrochamber 420 into a deaeration chamber 410 and a heating chamber 412. The deaeration chamber 410 is configured to deaerate water received by the dialysate circuit 400, and the heating chamber 412 is configured to heat water received by the dialysate circuit 400. The heating chamber 412 includes a temperature control thermistor 414 for monitoring the temperature of the heated water and a heater 416 to increase the temperature of the water received by the heating chamber 412. For example, if the temperature of the water received by the heating chamber 412 is below a threshold temperature, as detected by temperature control thermistor 414, the heater 416 can be used to heat the water above the threshold temperature. An air separator 418 is positioned downstream of the heating chamber 412 to further deaerate the flow of water as the degassing pump 404 pumps the water from the hydrochamber 420 to the container 104 and additionally towards the dialyzer 112.

The warmed and deaerated water flows from the air separator 418 to the container 104 containing the bicarbonate powder in order to form a bicarbonate solution. The inlet 208 of the container 104 is fluidly connected to the hydrochamber 420 of the dialysate circuit 400 allow water to be pumped from the hydrochamber 420 into the container 104 using the degassing pump 404.

The flow of fluid from the hydrochamber 420 into the container 104 is controlled by fill valves 442, 443 positioned along the dialysate circuit 400 upstream of the container 104. The fill valves 442, 443 is controlled by the processor 114 of the hemodialysis machine 106 to open and close in order to control the flow of warmed water into the container 104. For example, as will be described in further detail herein, the processor 114 controls the fill valve 442 to open and close based on signals received from a pressure sensor 444 configured to detect the pressure inside the container 104 and fill valve 443 is opened based on the temperature control thermistor 414 positioned along the dialysate circuit 400 upstream of the container 104. The pressure sensor 444 measures changes in pressure within the container 104 as fluid is provided from the hydrochamber 420 to the container 104 and as bicarbonate solution is removed from the container 104 to form dialysate.

The bicarbonate pump 432 is positioned along the dialysate circuit 400 downstream of the bicarbonate container 104. The bicarbonate pump 432 is configured to pump bicarbonate solution from the container 104, through a bicarbonate rinse chamber 460, through an air separation chamber 446, and towards balancing devices 454, 456. The air separation chamber 446 is located downstream of the container 104 and bicarbonate rinse chamber 460 and is configured to release any air contained within the bicarbonate solution withdrawn from the container 104 before mixing the bicarbonate solution with other fluids to form dialysate. The dialysate circuit 400 also includes a conductivity sensor 448 downstream of the container 104 and the bicarbonate rinse chamber 460 that is configured to sense the conductivity of the bicarbonate solution withdrawn from the container 104. The conductivity sensor 448 sends signals containing conductivity information to the processor 114. The conductivity information can be used to determine when bicarbonate levels of the solution withdrawn from the container 104 are below a threshold. For example, resultant of the amount of dried bicarbonate within the container becoming too low to maintain a fully saturated solution. The dialysate circuit 400 also includes a temperature sensor 450 that is downstream of the container 104 and measures the temperature of the bicarbonate solution withdrawn from the container 104 into the dialysate circuit 400. The temperature sensor 450 is connected to the processor 114 of the hemodialysis machine 106 and is configured to transmit temperature information to the processor 114.

The dialysate circuit 400 also includes an acid concentrate rinse chamber 462 and an acid concentrate pump 426. The acid concentrate rinse chamber 462 provides a reservoir for acid concentrate solution drawn into the hemodialysis machine 106. The acid concentrate pump 426 is configured to pump acid concentrate solution from the acid concentrate rinse chamber 462, through an air separation chamber 452, and into fluid line 464 where water, acid solution, and bicarbonate solution generated using the container 104 is mixed to form dialysate which enters into balancing chambers 454, 456. The air separation chamber 452 is located downstream of the acid concentrate rinse chamber 462 and is configured to release any air contained within the acid concentrate solution withdrawn from the acid concentrate rinse chamber 462 before mixing the acid concentrate solution with other fluids to form dialysate.

As bicarbonate solution and acid concentrate solution are withdrawn from the bicarbonate rinse chamber 460 and the acid concentrate rinse chamber 462 by the bicarbonate pump 432 and the acid concentrate pump 426, respectively, the bicarbonate solution and acid concentrate solution mix with one another along a fluid line 464 of the dialysate circuit 400 upstream of balancing chambers 454, 456 in order to form dialysate. The fresh dialysate generated along the fluid line 464 by combining the bicarbonate solution and the acid concentrate solution is drawn into a pair of balancing devices 454, 456 by the operation of a dialysate flow pump 495.

The balancing devices 454, 456 each include a spherical chamber that is divided into a first chamber half and a second chamber half by a flexible membrane. As fluid flows into the first chamber halves of the balancing devices 454, 456, fluid is forced out of the second chamber halves of the balancing devices 454, 456, and vice versa. Valves are used to control the flow of dialysate into and out of the balancing devices 454, 456 such that as fresh dialysate is flowing into the first chamber halves of balancing devices 454, 456, spent dialysate is flowing out of the second chamber halves of balancing device 454, 456, and vice versa. In this way, the two balancing chambers double the volume production and are designed to work in tandem.

This balancing device construction and alternating flow of fresh and spent dialysate helps to ensure that the volume of fluid entering the balancing devices 454, 456 is equal to the volume of fluid exiting the balancing devices 454, 456. This helps to ensure that the volume of fresh dialysate entering the dialysate circuit is equal to the volume of spent dialysate exiting the dialysate circuit during treatment, as described in greater detail below.

During hemodialysis, fresh dialysate passing through the balancing devices 454, 456 is directed to the dialyzer 112 through a dialysate filter 474 configured to filter the fresh dialysate received from the balancing devices 454, 456 prior to providing the dialysate to the dialyzer 112. One example of such a dialysate filter 474 is the DIASAFE® plus dialysis fluid filter available from Fresenius Medical Care.

After filtration by dialysate filter 474, the fresh dialysate flows through a conductivity cell 470 and a temperature monitor thermistor 472. The conductivity cell 470 and temperature monitor thermistor 472 report the temperature and temperature compensated dialysate conductivity to processor 114 to ensure the fresh dialysate is in the appropriate temperature and conductivity range. This fresh dialysate enters a second filter 576, which can be used to generate a twice filtered dialysate for the purpose of generating substitution fluid, and then dialyzer 112. One example of such a dialysate filter 476 is the DIASAFE® plus dialysis fluid filter available from Fresenius Medical Care. During hemodialysis, a bypass valve 475 and substituate valve 477 are closed and a dialyzer inlet valve 579 is open in order to direct the flow of dialysate through the dialysate filters 474, 476 to the dialyzer 112. During hemofiltration and hemodiafiltrations where a substitution fluid pump is used to actively generate substitution fluid, substituate valve 477 is open and substitution fluid generated from dialysate filter 476 enters the via the arterial patient line 110 and/or the venous patient line 111.

During hemodialysis, spent dialysate flows out of the dialyzer 112 along a spent dialysate line 480 of the dialysate circuit 400. A pressure sensor 486 located along the spent dialysate line 480 connecting the dialyzer 112 to an air separation chamber 493 is adapted to measure the pressure of the spent dialysate exiting the dialyzer 112. Any of various different types of pressure sensors capable of measuring the pressure of the spent dialysate passing from the dialyzer 112 to the air separation chamber 493 can be used.

The spent dialysate exiting the dialyzer 112 collects in the air separation chamber 493. An air sensor coupled to the air separation chamber 493 is used to detect air contained within the spent dialysate, and the air separation chamber 493 vents off any air contained with the spent dialysate.

The dialysate flow pump 495 is configured to pump the spent dialysate from the air separation chamber 493 through a fluid line to the second chamber halves of the balancing devices 454, 456. As previously discussed, the flow of spent dialysate into the balancing devices 544, 456 is controlled by valves that alternate the flow of spent dialysate into and out of the balancing devices 454, 456. As the second chamber halves of the respective balancing devices 454, 456 fills with the spent dialysate, fresh dialysate within the respective first chamber halves is expelled towards the dialyzer 112. Subsequently, as the first chamber halves of the respective balancing device 454, 456 is refilled with fresh dialysate, the spent dialysate is forced out the respective second chamber halves toward drain line 481 to the drain.

Still referring to FIG. 4, an ultrafiltration pump 497 is operatively connected to an ultrafiltration line 491 of the dialysate circuit 400, and when the ultrafiltration pump 497 is operated, spent dialysate can be pulled from the air separation chamber 493 and directed to the drain line 481 via the ultrafiltration line 491. Operation of the ultrafiltration pump 497 causes increased vacuum pressure within the line connecting the air separation chamber 493 to the dialyzer 112, and thus creates increased vacuum pressure within the dialyzer 112. As a result of this increased vacuum pressure within the dialyzer 112, additional fluid is pulled from the blood circuit into the dialysate circuit 400 across the semi-permeable structure (e.g., semi-permeable membrane or semi-permeable microtubes) of the dialyzer 112. Thus, the ultrafiltration pump 497 can be operated to remove excess fluid from the patient.

Figure 5:
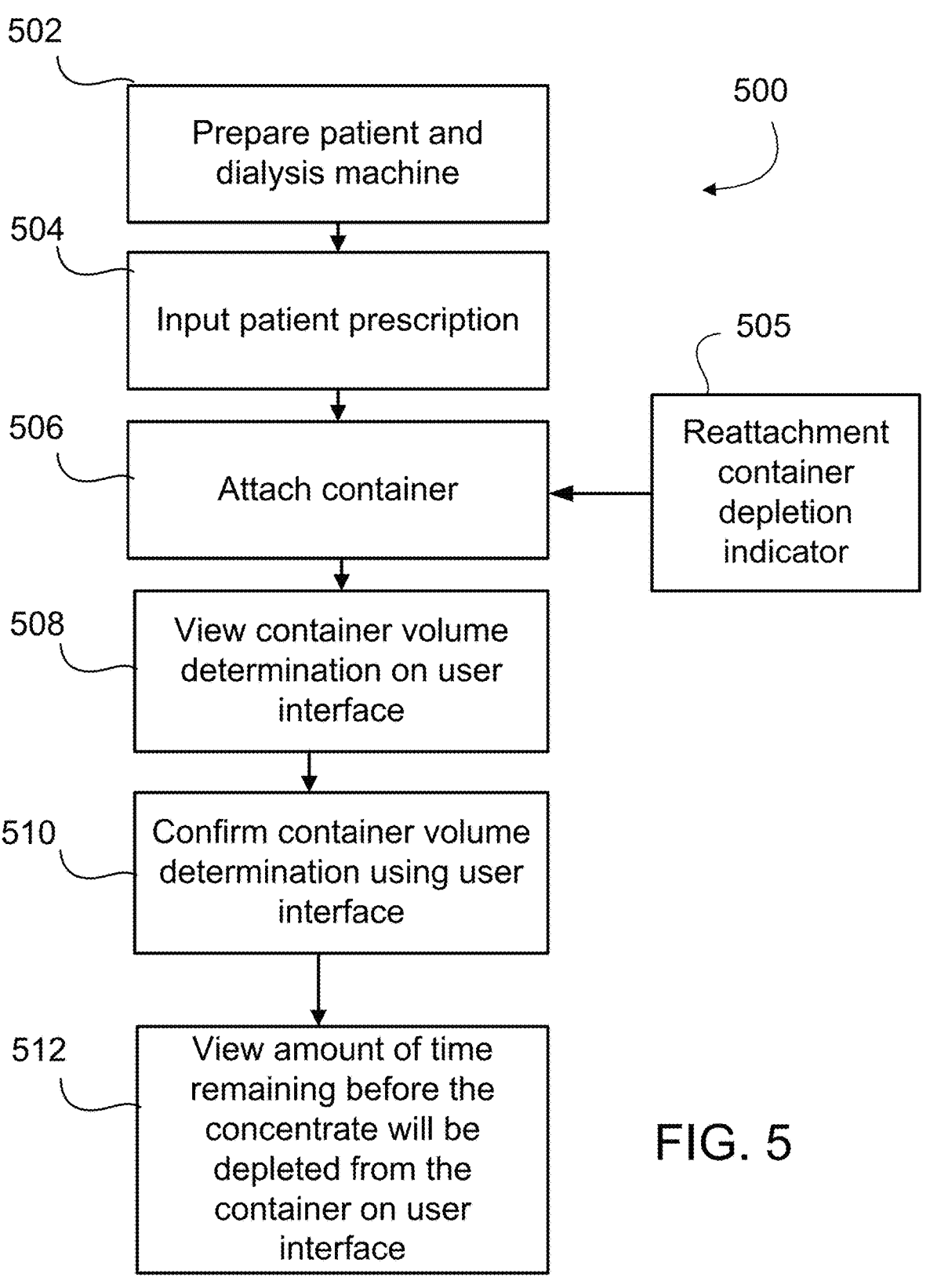
FIG. 5 depicts a procedure performed by an operator of a dialysis machine.

A process 500 performed by an operator to attach a container 104 to the hemodialysis machine 106 will now be described with reference to FIG. 5. In preparing the hemodialysis system 100 for treatment, an operator prepares the dialysis system (502) and inputs the prescription of the patient (504), including a dialysate flow rate, a bicarbonate concentration level, a treatment time, and if applicable a substitution fluid pump rate. As previously discussed, in some implementations, the prescription information is provided to the hemodialysis machine 106 using the user interface 102 of the hemodialysis machine 106 or alternatively in some implementations is provided wirelessly or through use of a patient card with preloaded prescription information. Once prescription information is input into the machine prior to starting the hemodialysis treatment (504) or after receiving a container depletion indicator during treatment (505), the operator attaches a new container 104 containing bicarbonate to the hemodialysis machine 106 (506). The container 104 is connected to the hemodialysis machine 106 using the connector 204 shown in FIG. 2, and the status of the container absence or presence and additionally the status of the container door being opened or closed is provided to processor 114 which ensures the filling of container 104 only occurs when the container 104 is installed and the container door is fully closed.

Once the container 104 is attached to the hemodialysis machine 106, the hemodialysis machine 106 performs a test to determine the volume of the container 104 and displays the determined volume of the container 104 on the user interface 102 of the hemodialysis machine (508). In some implementations, the container 104 is attached to the hemodialysis machine 106 and the testing procedures for determining the container volume are performed before the hemodialysis machine 106 has performed a routine self-test performed as part of the initial setup of the machine. In some implementations, the container 104 is attached to the hemodialysis machine 106 and the testing procedure for determining the container volume are performed during treatment. In some implementations, the hemodialysis machine 106 can prompt the user to attach a bicarbonate container before the routine self-test begins and then maximize the dialysate flowrate during the container volume determination testing procedure to minimize setup time.

The operator can be presented with a volume determination prompt on user interface 102 of the hemodialysis machine to confirm or adapt the volume of the container 104 determined by the hemodialysis machine 106 (510). For example, if the volume of the container 104 determined by the hemodialysis machine 106 correctly corresponds to the volume printed on the container 104, the user can use the user interface 300 to confirm the volume of the bicarbonate container 104 displayed on the user interface 300. If the volume of the container 104 determined by the hemodialysis machine 106 and displayed on the user interface 300 does not correspond to the volume printed on the container 104 coupled to the hemodialysis machine 106, the user can use user interface 300 to update the volume of the bicarbonate container 104 to reflect volume indicated on the container 104.

In some implementations, the dialysis machine determines that a container has been attached to the machine using sensors that can detect the open/close state of the container door, and also the connect/no connect status of the bag. For example, the sensors can measure four conditions (A-D). These conditions are (A) Open door, no bag; (B) Open door, with bag; (C) Closed door, no bag; and (D) Closed door, with bag. In some examples, the filling temperature is checked to allow for filling to take place if condition D is determined. In some examples, the filling temperature is checked to allow for filling to take place only if condition D is determined.

FIG. 6 depicts a process 600 performed by the hemodialysis machine 106 to determine the volume of the container 104 coupled to the hemodialysis machine 106. After the container 104 has been coupled to the hemodialysis machine 106, the hemodialysis machine 106 is controlled to initiate a container volume testing procedure by flowing water from the hemodialysis machine 106 (into the container 104 and staring a timer of the hemodialysis machine 106 (602). In some examples, the machine includes a dialysate temperature setpoint and the setpoint is used to control the temperature of the heater.

Referring to FIG. 4, after attaching the container 104 to the hemodialysis machine 106, based on the signals received from the temperature control thermistor 414, the processor 114 determines when the temperature of the water needed to generate bicarbonate solution is within an acceptable temperature range to be allowed into container 104, and in response to detecting that the deaerated water flowing out of the heating chamber 412 is at the temperature required to dissolve the bicarbonate contained in the container 104, valve 443 is placed in an open state and valve 442 downstream of the air separator 418 is opened to allow fluid to flow along the fluid line 445 towards the bicarbonate container 104. During the testing period, warmed and deaerated water flowing along the fluid line 445 flows into the bicarbonate container 104. The rate of water flowing into to the hydrochamber 420 is controlled based on the dialysate flow rate, and if applicable the substitution fluid pump rate, provided in the treatment prescription parameters received by the hemodialysis machine 106, and has an indirect effect on the filling of bicarbonate container 104 based on the associated pressure of dialysate circuit 400.

The pressure sensor 444 monitors the pressure within the container 104 as the water flows into the container 104 to dissolve the powdered bicarbonate contained within the container 104 (604). For example, as water initially flows from the hydrochamber 420 into the container 104 to fill the container 104 and dissolve the powdered bicarbonate within the container 104, the corresponding increase in pressure within the container 104 is monitored by the pressure sensor 444.

Figure 8:
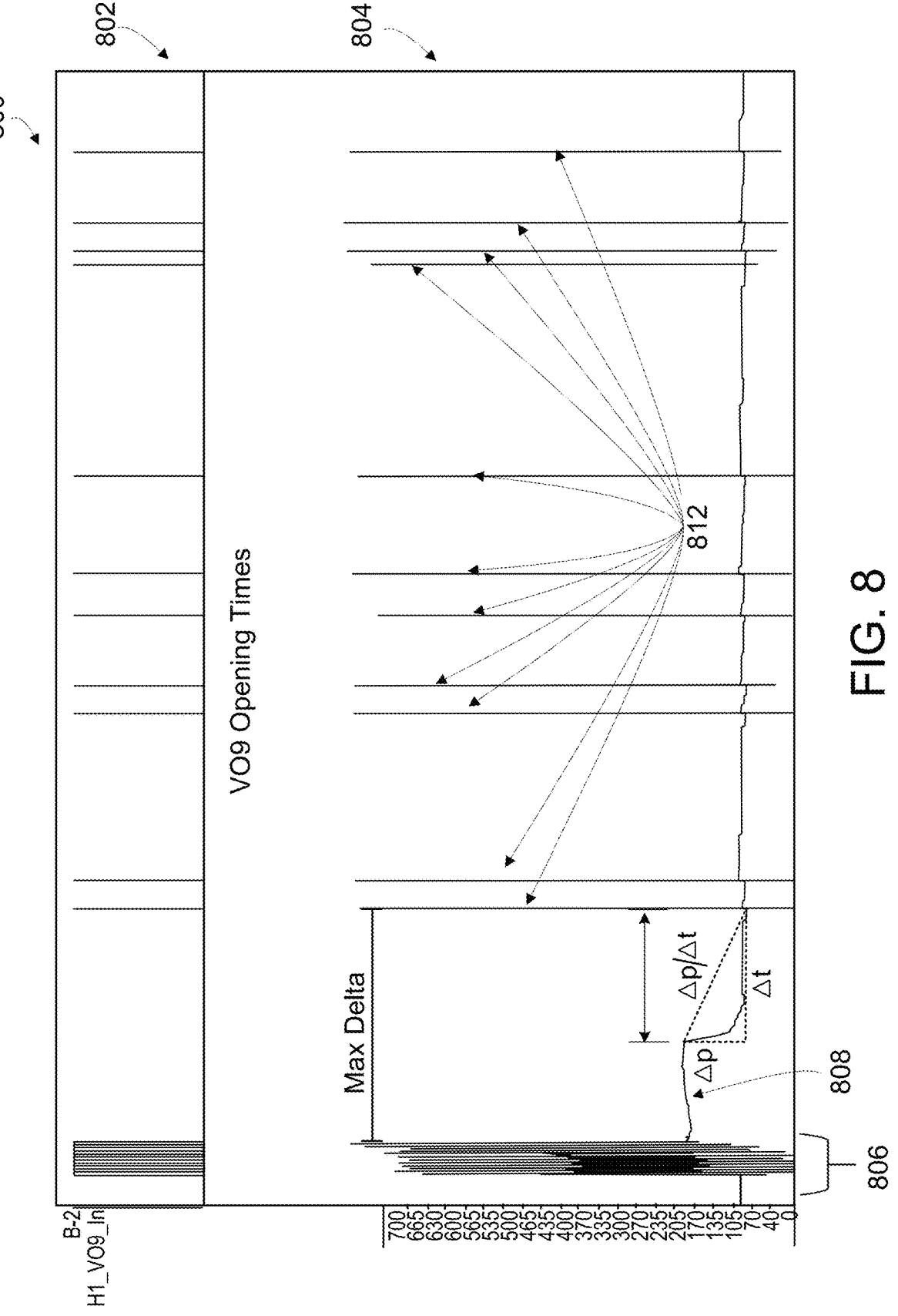
FIG. 8 depicts pressure signals and valve status signals during a testing period for determining the volume of a container coupled to a dialysis machine.

FIG. 8 depicts the results of a testing period 800 analyzing the valve signals 802 received from the valve 442 indicating the valve state as open or closed and the pressure signals 804 received from the pressure sensor 444 while performing a volume test for a container 104 that is a 900 g bicarbonate bag ("bibag") using a prescribed dialysate flow rate of 300 ml/min to achieve a prescribed bicarbonate solution concentration of 26 mEq/L. At the beginning of the testing period, an initial filling procedure 806 is performed in which the valve 442 repetitively opens and closes, with the duration of each opening based on the detected pressure 804 measured by processor 114 before (e.g., immediately before) valve 442 opening is initiated. For example, the valve has an opening duration based on the pressure measured before opening and a cyclic approach is used to achieve the final threshold 150 mmHg for 3 seconds.

The valve 442 is controlled to reopen once the valve 442 had closed for a brief duration to allow the pressure 804 has stabilized to dictate the duration of time for the next valve 442 opening, which allows additional fluid to be provided to the container 104. As can be seen based on the valve signals 802 and pressure signals 804 depicted in FIG. 8, the initial filling process of closing and reopening the valve 442 is repeated multiple times until the pressure within the container 104 achieves an initial fill completion pressure threshold for a predetermined amount of time, indicating that the initial filling of the container 104 is complete. For example, as can be seen in FIG. 8, once the pressure within the container 104 is maintained at 150 mmHg for at least 3 seconds while the valve 442 is closed, the processor 114 identifies the initial filling of the container as being complete and the valve 442 remains closed until either a baseline fill 812 of the container 103 is required, or a subsequent initial fill routine is triggered resultant of a dramatic drop in pressure 804 being reported to processor 114 as will be described in further detail herein. In some implementations, a second initial fill is automatically forced after completion of the first initial filling period with a concurrent withdrawal of fluid from the container 104 to result in a higher amount of fluid to be introduced.

After completion of the initial filling procedure 806, the pressure sensor 444 continues to monitor the pressure within the container and after a period of no filling 808, bicarbonate solution is drawn out of the container into the dialysate circuit (as described above with reference to FIG. 4). As bicarbonate solution is drawn out of the container 104, the pressure within the container 104 decreases. When the pressure sensor 444 detects that the pressure 804 within the container 104 is below a baseline fill pressure threshold 810, the hemodialysis machine 106 controls valve 442 to open in order to perform a baseline fill cycle 812. For example, as depicted in FIG. 8, the valve 442 is controlled to open whenever the pressure sensor 444 detects that the pressure 804 within the container 104 is below 90 mmHg for a set duration of time. This process is repeated throughout the testing period to perform multiple baseline fill cycles 812. In some implementations, the duration of the testing period is until the first baseline fill is performed. In some implementations, the testing period continues until between up to 30 baseline fill cycles 812 are completed.

For example, if the hemodialysis machine 106 has a maximum dialysis flowrate and a 900 g bibag is detected resultant of the 2 initial fill routines being triggered, monitoring baseline fills becomes unneeded. In some examples, monitoring of baseline fills is performed (e.g., only performed) if the other variables don't provide a determinative assessment of the container size. In some examples, baseline fills, which can take longer to assess, should be used if other more immediate variables don't provide a clear assessment.

Referring back to FIG. 6, throughout the testing period, the pressure sensor 444 transmits the pressure signals 804 indicating the pressure within the container 104 to the processor 114 of the hemodialysis machine 106 and the valve 442 upstream of the container 104 sends signals 802 indicating the open versus closed state of the valve 442 to the processor 114 (606). The hemodialysis machine 106 uses signals 802, 804 to determine a set of fill parameters corresponding to the container 104 based on the pressure signals received from the pressure sensor 444 and the valve state signals received from the valve 442 during the testing period (608). For example, the hemodialysis machine 106 can determine the fill parameters as soon as the hemodialysis machine 106 is capable and not necessarily at the end of a test.

Figure 9:
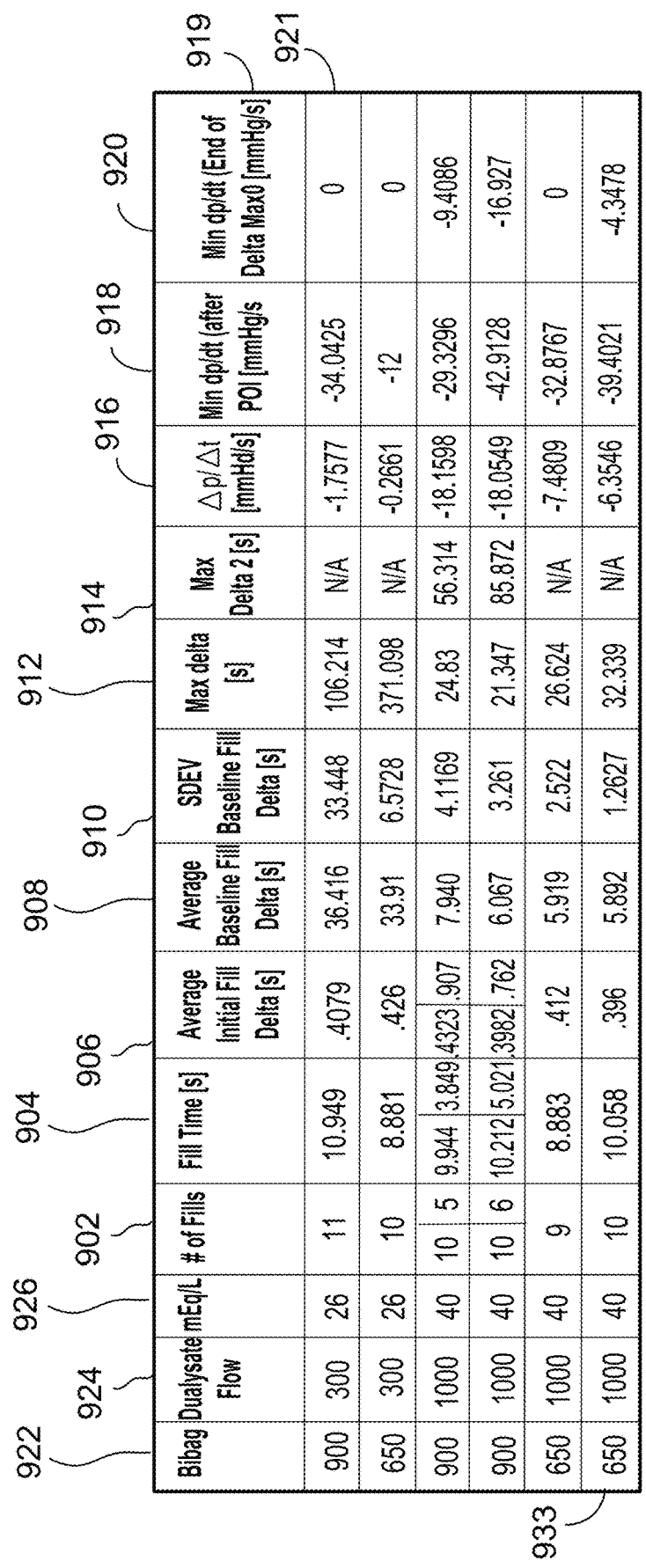
FIG. 9 depicts a table of fill parameters determined based on pressure signals generated by a pressure sensor measuring the pressure within a container coupled to a dialysis machine during a testing period.

FIG. 9 depicts a table 900 summarizing the fill parameters 902-920 for multiple container volume testing procedures using both 650 g and 900 g bicarbonate bags ("bibag") with two example prescriptions: 1) dialysate flow rate of 300 ml/min and prescribed bicarbonate solution concentration of 26 mEq/L, including the fill parameters determined based on the signals generated in the testing period 800 depicted in FIG. 8 utilizing a 900 g bibag container, and 2) dialysate flow rate of 1000 ml/min and prescribed bicarbonate solution concentration of 40 mEq/L.

As can be seen in FIG. 9, multiple fill parameters 902-920 can be determined based on the pressure signals 804 and valve state signals 802 generated during the container volume testing period and received by the processor 114 of the hemodialysis machine 106. Fill parameters that can be determined based on the pressure signals and valve state signals generated during a container volume test include, but are not limited to, a total number of fills (i.e., valve openings) performed during the initial fill procedure 902, an amount of time during the initial fill procedure where valve 442 is open 904, an average of the amount of time elapsed between each closing and reopening of valve 442 during the initial fill procedure 906, an average of the amount of time elapsed between each closing and reopening of valve 442 during baseline fill cycles 908, a standard deviation of the amount of time elapsed between each closing and reopening of valve 442 during baseline fill cycles 910, the amount of time elapsed between the completion of the initial fill procedure and the first valve 442 opening resultant of a baseline fill 912 ("Max Delta"), Additional fill parameters 916, 918, 920 can be determined based on the rate of change of pressure within the container starting at a point during the testing period herein referred to as a "point of interest". The "point of interest" represents the point occurring after the completion of the initial fill procedure and before the start of the first baseline fill cycle corresponding to a notable decrease in pressure resultant of the initiation of fluid being pulled from the bicarbonate container 104. In some implementations, the point of interest corresponds to a point during the testing period after completion of the initial fill procedure when the rate of pressure change within the container 104 detected by the pressure sensor 444 exceeds a predetermined threshold. Alternatively, the point of interest can be determined by the signals received from processor 114 from bicarbonate pump 432 occurring between the completion of the initial fill procedure and the first baseline fill, or the point of interest can be determined using both an assessment of the rate of pressure change within container 104 and the signals received from processor 114 from bicarbonate pump 432.

As is discussed in further detail below, upon detection of the first baseline fill during the testing period, the pressure signals 804 collected by processor 114 during the time after the completion of the initial fill procedure up to the first baseline fill are assessed to generate a point of interest. Upon generation of the point of interest, the following fill parameters can be assessed: the rate of change of pressure within the container occurring between the point of interest and the start of the first baseline fill cycle 916 ("Δp/Δt"), a minimum valve for the instantaneous rate of change in pressure occurring immediately after the point of interest 918 ("min Δp/Δt after POI"), and the minimum value for the instantaneous rate of change of pressure measured immediately preceding the first baseline fill 920 (i.e., at the end of the "Delta Max" period of testing). The point of interest is correlative with the initiation time of the bicarbonate pump as it starts pulling fluid from the container.

Figure 12:
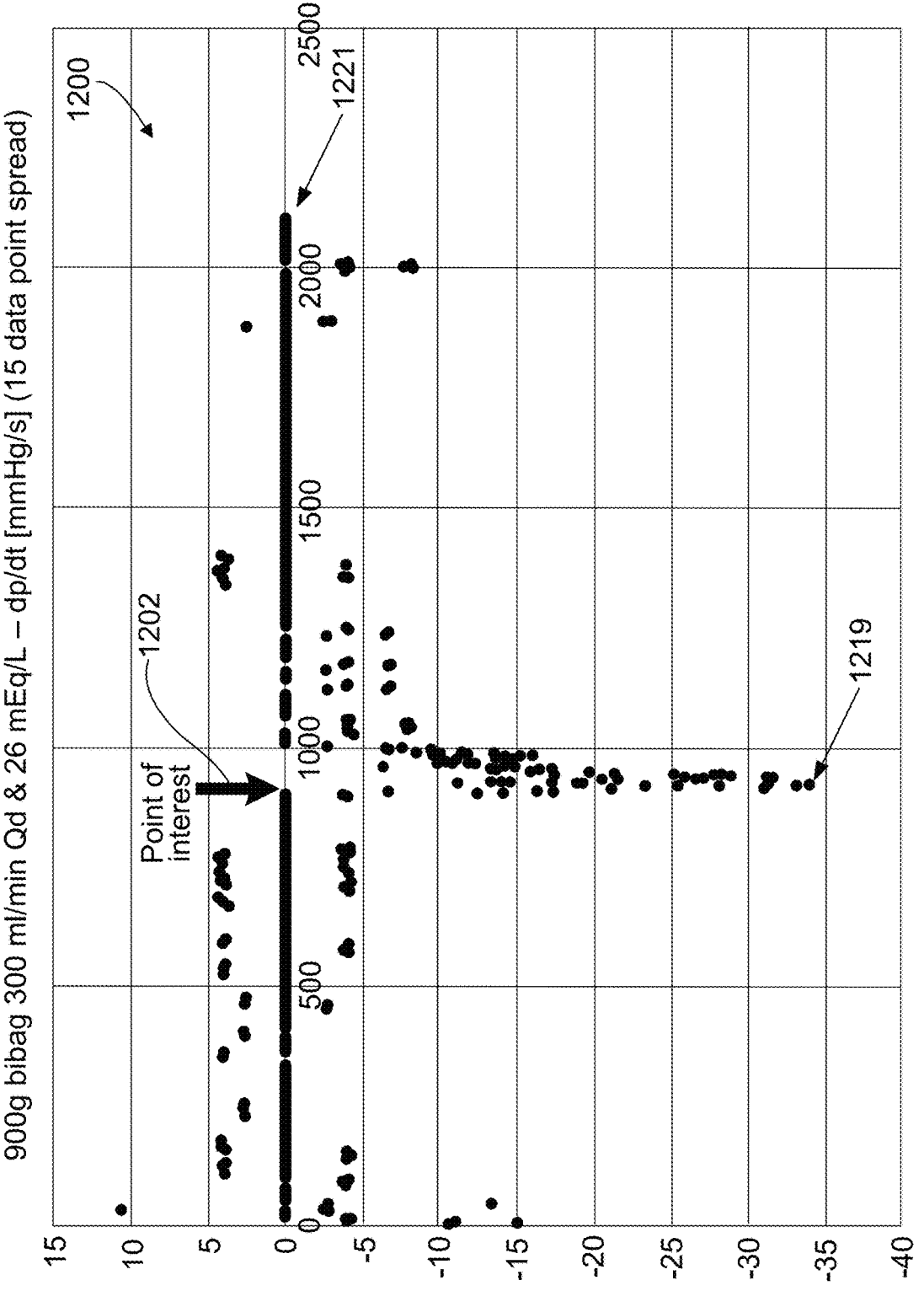
FIGS. 12 and 13 depict charts of the rate of change of pressure within a container coupled to a dialysis machine over time during a testing period.

FIG. 12 is a chart 1200 of the instantaneous rate of change of pressure within the container 104 as measured by the pressure sensor 444 during the testing period 800 depicted in FIG. 8. The pressure data was generated though generation of a change of pressure over time between 15 data points for all 15 datapoint sets between the point of interest and the first baseline fill. As can be seen in FIGS. 9 and 12, the min Δp/Δt after POI fill parameter 918 corresponding to the minimum value for the instantaneous rate of change of pressure within the container 104 occurring immediately after the point of interest 1202 is about −34 mmHg/s (field value 919, data point 1219). In addition, the fill parameter 920 corresponding to the minimum value for the instantaneous rate of change in pressure measured immediately preceding the first baseline fill is 0 (field value 921, data point 1221).

Figure 13:
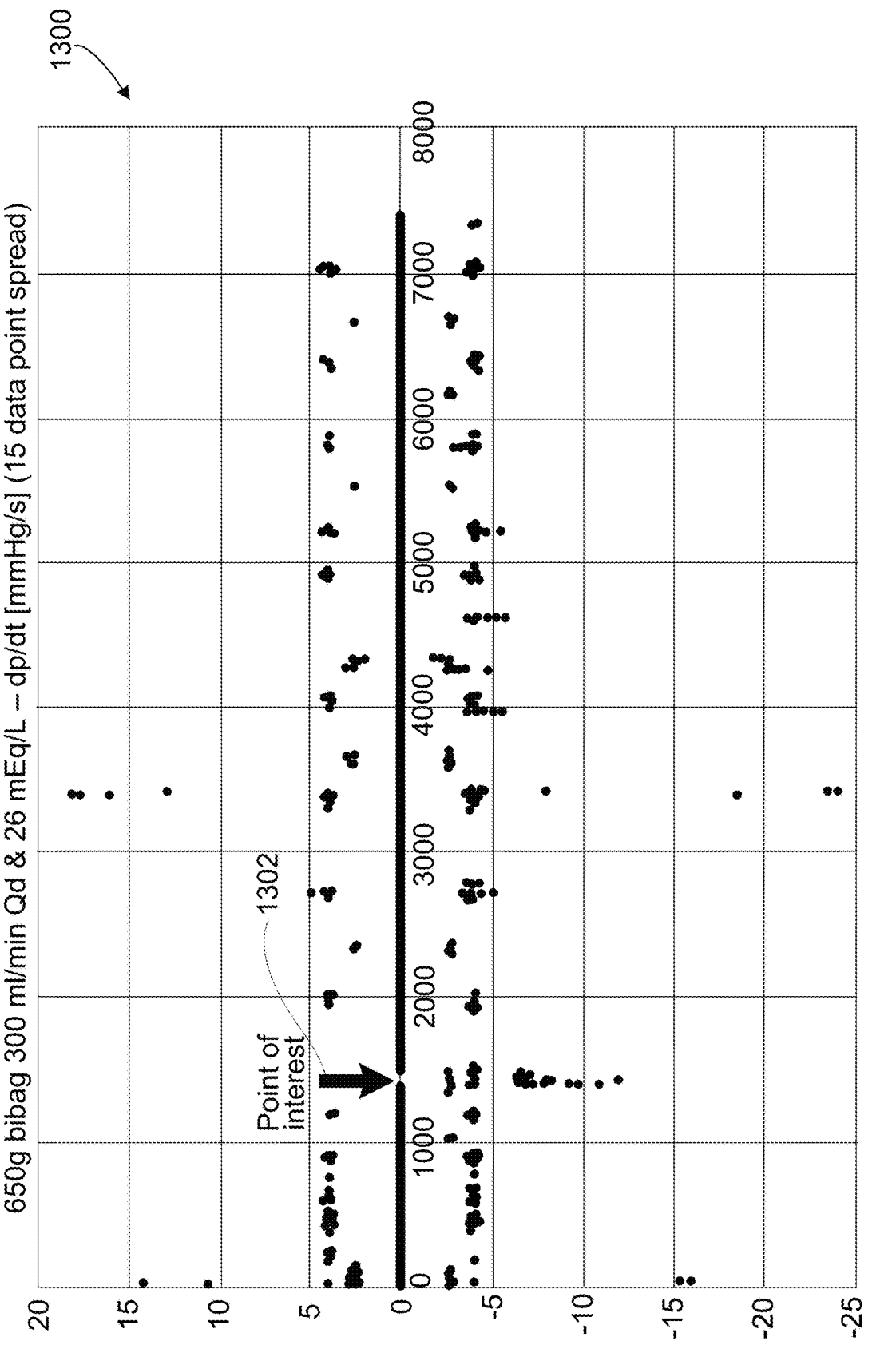

As can be seen in FIG. 9, at lower flow rates (e.g., dialysate flow rates less than 500 mL/min), the min Δp/Δt after POI fill parameter 918 corresponding to the minimum instantaneous rate of change of pressure occurring within the container 104 immediately after the point of interest demonstrates a stronger degree of correlation with the size of the container 104 than as observed at higher dialysate flow rates. For example, as previously discussed and as can be seen in FIGS. 9 and 12, the min Δp/Δt after POI fill parameter 918 corresponding to instantaneous rate of change of pressure within the container 104 at the point of interest 1202 is about −34 mmHg/s for a 900 g bibag being filled based on a 300 mL/min dialysate flow rate 924. In contrast, as can be seen in the table 900 of FIG. 9 and the chart 1300 in FIG. 13 depicting the instantaneous rate of change of pressure within a 650 g bibag being filled with water using a prescribed dialysate flow rate of 300 ml/min and prescribed bicarbonate solution concentration of 26 mEq/L, the min Δp/Δt after POI fill parameter 918 corresponding to minimum instantaneous rate of change of pressure occurring within the container after (e.g., immediately after) the point of interest 1302 is about −12 mmHg/s.

For some combinations of container size 922 and dialysate flow rate 924, a second initial filling procedure is triggered and identified as a fill parameter. As can be seen in FIG. 9, this only occurred with 900 g bibag containers at a dialysate flow rate of 1000 ml/min. Additionally, the minimum value for the instantaneous rate of change of pressure measured immediately preceding the first baseline fill 920 also provided more correlative behavior for prediction of container size at the higher machine dialysate flow rate setting. Accordingly, in some embodiments the fill parameter 902 corresponding to total number of fills (i.e., valve openings) performed during the initial fill procedure has two components: 1) total number of valve openings and 2) total number of initial fill routines. In some embodiments, due to fill parameters 902 and 920 being a more correlative indicator of the container size 104 at higher dialysate flow rate settings, the dialysate flow rate is automatically adjusted during machine preparation to a maximum rate during the testing period as this has the benefit of not only providing a strong correlative factor of container size, but also would minimize the time for the machine to establish a stabilized dialysate conductivity which has the potential to reduce start-up time. Such a modification to the machine dialysate flow rate for the testing period during treatment though feasible, would likely not be desirable as this adaption of the prescription dialysate flow rate could force the necessity of placing the machine into bypass which would add delay to treatment.

Figure 10:
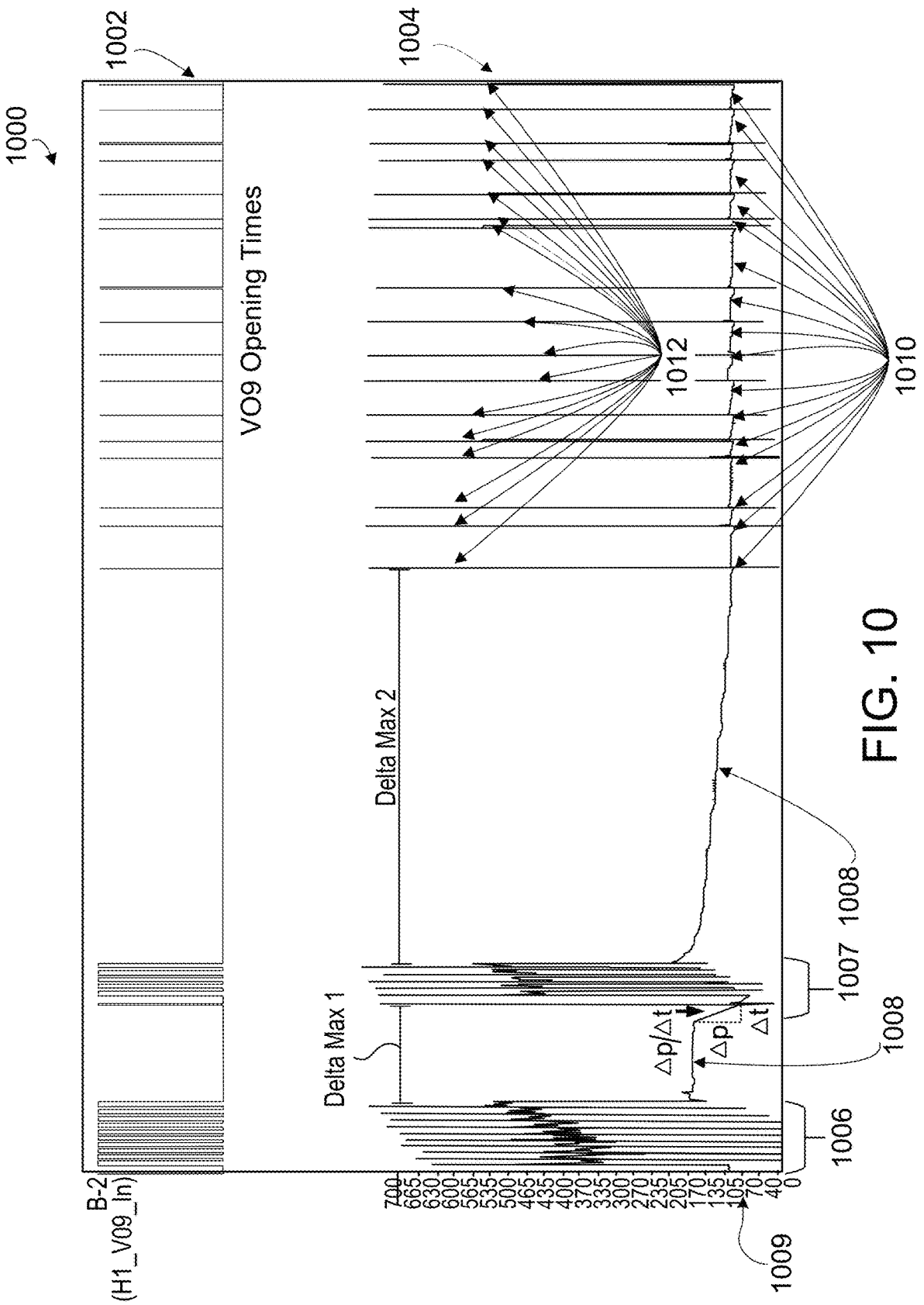
FIGS. 10 and 11 depict pressure signals and valve status signals generated during other example testing periods for determining the volume of a container coupled to the dialysis machine.

Additionally, for the larger 900 g bibag containers, independent of the prescribed dialysate flow rate and prescribed bicarbonate solution concentration a larger rate of change of pressure over time within the container 104 occurring between the point of interest and the start of the first baseline fill cycle 916 ("Δp/Δt") can be discerned. For example, FIG. 10 depicts a filling procedure 1000 for a 900 g bibag container using a prescribed dialysate flow rate of 1000 ml/min and a prescribed bicarbonate solution concentration of 40 mEq/L. As can be seen in FIG. 10, a first initial fill procedure 1006 is performed, ending once the pressure 1004 within the container 104 is maintained at 150 mmHg for at least 3 seconds while the valve 442 is closed. As further illustrated in FIG. 10, after completion of the first initial fill procedure 1006, the pressure 1004 within the container quickly drops below an initial fill trigger pressure threshold pressure 1009 due to the larger bibag size and the high dialysate flow rate, which causes the hemodialysis machine 106 to initiate a second initial fill procedure 1107 before performing any baseline fill cycles 1012. For example, in response to detecting that the pressure within the container has dropped below an initial fill trigger pressure threshold pressure 1009 of 70 mmHg, the hemodialysis machine 106 controls the valve 442 to operate to perform a second initial fill procedure 1007 similar to the first initial fill procedure 1006 before performing any baseline fill cycles 1012. The second initial fill procedure 1007 is complete when the pressure 1002 within the container 104 is maintained at initial fill completion pressure threshold 1008 (e.g., 150 mmHg) for a predetermined amount of time (e.g., about 3 seconds). After completion of the second initial fill procedure 1007, the valve 442 is controlled to perform a baseline fill cycle 1012 each time the pressure sensor 444 detects that the pressure 1002 within the container 104 is below a baseline fill pressure threshold 1010 (e.g., 90 mmHg). As can be seen in FIG. 10, multiple baseline fill procedures 1012 are performed during the testing period in order to maintain the volume of fluid within the container 104 that would be necessary to perform the prescribed treatment.

Figure 11:
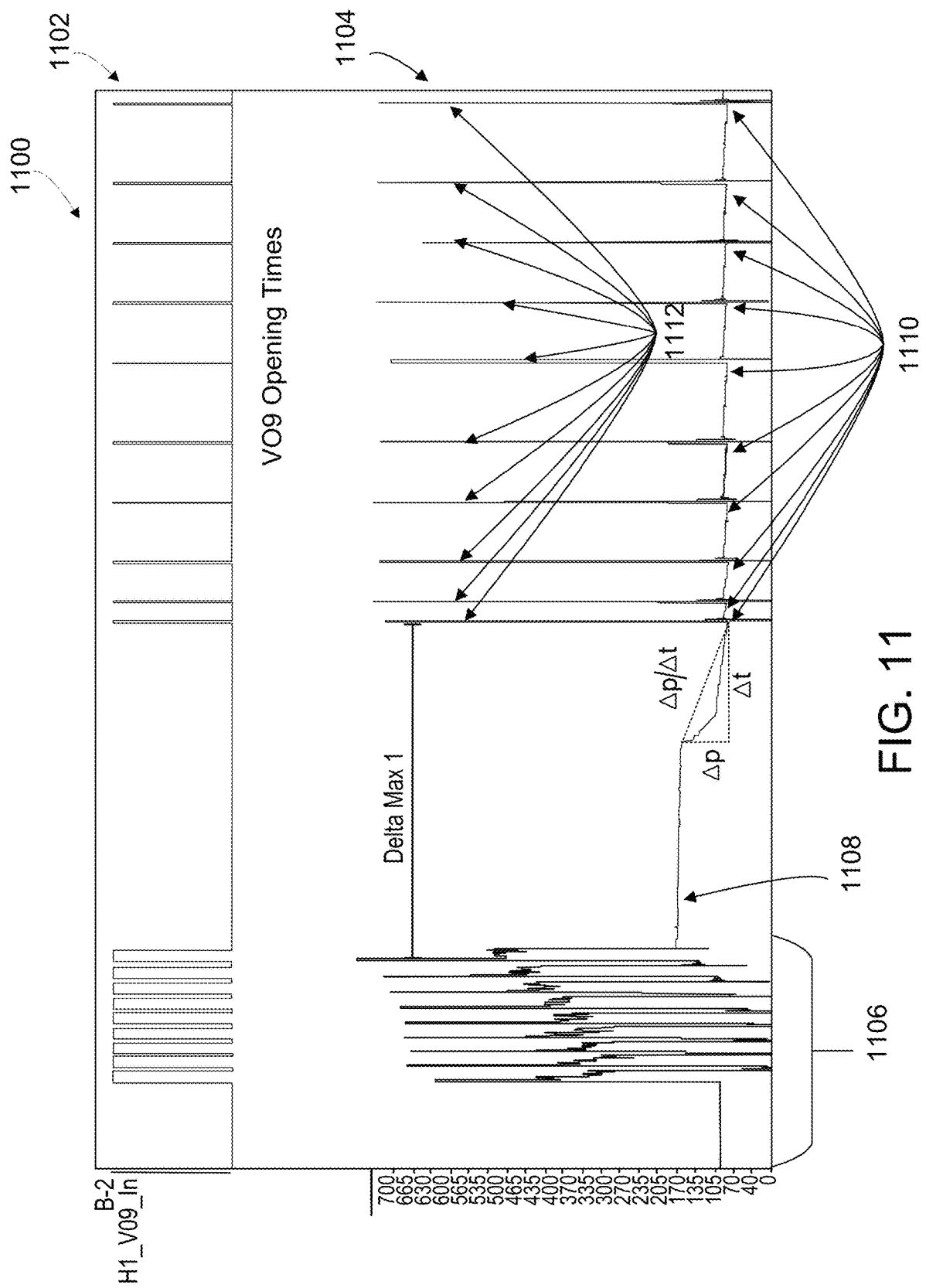

In contrast, FIG. 11 depicts a filling procedure 1100 that implements the same prescribed dialysate flow rate of 1000 ml/min and bicarbonate solution concentration of 40 mEq/L as that implemented in the filling procedure 1000 depicted in FIG. 10, but is implemented using a smaller, 650 g bibag container (compared to the 900 g bibag in FIG. 10). As can be seen in FIG. 11, while the dialysate flow rate and bicarbonate solution concentration for the filling procedure 1100 depicted in FIG. 11 are the same as the dialysate flow rate and bicarbonate solution concentration used for the filling procedure 1000 depicted in FIG. 10, a second initial filling procedure is not triggered during the filling procedure 1100 due to the use of a smaller container 104 (650 g bibag compared to 900 g bibag). Rather, after the initial fill procedure 1106 is complete, as determined based on detecting that the pressure 1102 within the container 104 is maintained at initial fill completion pressure threshold 1108 (e.g., 150 mmHg) for a predetermined amount of time (e.g., about 3 seconds) with the valve 442 closed, the valve 442 is controlled to open in order to perform a baseline fill procedure 1112 in response to detecting that the pressure 1102 within the container 104 is below a baseline fill pressure threshold 1110 (e.g., 90 mmHg). As described above with reference to FIGS. 8 and 10, the valve 442 is controlled to perform multiple baseline fill cycles 1112 during the testing period to maintain the pressure in the container 104 above 90 mmHg.

For testing periods in which a second initial fill procedure 1007 is triggered, such as the testing procedure 1000 depicted in FIG. 10, additional fill parameters can be identified. For example, as depicted in FIG. 9, for containers with a volume 922 corresponding to 900 g bibags testing using a 1000 mL/min dialysate flow rate 924 and 40 mEq/L bicarbonate concentration solution, a fill parameter corresponding to the amount of time elapsed between the completion of the second initial fill and the first baseline fill ("Max Delta 2") 914 is identified, and the Max Delta parameter 912 corresponds to the amount of time elapsed between the end of the of first initial fill procedure 1006 and the start of the second initial fill procedure 1007. In addition, as depicted in FIG. 9, for filling procedures that result in a second initial fill procedure, the fill parameter 902 includes a first number of fills corresponding to the first initial fill procedure 1006 and a second number of fills corresponding to the second initial fill procedure 1007 and as discussed above can also contain a count of the total number of initial fill routines triggered during the testing period. Other fill parameters impacted by the detection of a second initial fill routine 1007 include the amount of time during the initial fill procedure where valve 442 is open 904, as well as the average of the amount of time elapsed between each closing and reopening of valve 442 during the initial fill procedure 906.

As a result of the relationship between the volume of the container 104 and the various fill parameters 902-920, the volume of the container 104 can be determined based on the fill parameters measured for the container 104 during the testing period. Referring again to FIG. 6, once the container volume testing procedure is complete and the fill parameters for the container are determined, the volume of the container 104 is automatically determined based on two or more of the fill parameters identified for the container (610). For example, the volume of the container 104 can be determined based on comparing two or more of the fill parameters determined for the container 104 to corresponding reference fill parameters for different container sizes 922 being filled at the corresponding dialysate flow rate 924 and bicarbonate concentration settings 926 that were used to test the container 104.

In some embodiments, these reference values are based on an initial machine calibration with new containers of the available sizes supported by the machine placed on the machine at one or more combinations of dialysate flowrate and bicarbonate solution concentration, the values obtained on the machine from actual testing periods where the operator affirms the correct container 104 size was detected, or a combination thereof.

By utilizing at least two fill parameters to identify the volume of the container 104, rather than a single fill parameter, the accuracy of the volume determination is improved. For example, an algorithm can be applied to two or more of the fill parameters to determine the volume of the container 104. Equation 1 below provides an example algorithm that can be applied to two or more fill parameters in order to determine the volume of the container:

$$(\text{Fill Parameter 1 Threshold Exceeded})*(1/N \text{ Parameters}) + (\text{Fill Parameter 2 Threshold Exceeded})*(1/N \text{ Parameters}) + \dots (\text{Fill Parameter } N)*(1/N \text{ Parameters}) = \text{Container Volume Determination} \qquad \text{Equation 1:}$$

Using equation 1 above, each fill parameter determined for a container 104 based on the pressure signals and valve state signals generated during a testing period is compared to a corresponding fill parameter threshold. If the fill parameter determined for the container exceeds the corresponding fill parameter threshold, a 1 is assigned for the fill parameter. Conversely, if the fill parameter does not exceed the corresponding parameter threshold, a −1 is assigned to the fill parameter. Using the assigned values, the equation above can then be implemented to determine whether the container corresponds to a 900 g bibag or a 650 g bibag, with positive sums corresponding to a 900 g bibag and negative sums corresponding to a 650 g bibag. In some examples, the thresholds are dependent on the dialysate flowrate & bicarbonate setting as these both impact the bicarbonate pump speed which draws fluid from the bicarbonate container.

An example volume determination using equation 1 above is shown below in equation 2 and equation 3. In this example, the final row of FIG. 9 933 is used with the following thresholds for a container determination at a prescription dialysate flow rate of 1000 ml/min and a prescription bicarbonate concentration setting of 26 mEq/L: Fill Time [s] Threshold—9.7 seconds, Average Baseline Fill Delta [s] Threshold—6.0 seconds, SDEV Baseline Fill Delta [s] Threshold—3 seconds, and Max Delta [s] Threshold—25 seconds.

$$(\text{Fill Time [s] Threshold Exceeded})*(\tfrac{1}{4}) + (\text{Average Baseline Fill Delta [s] Threshold Exceeded})*(\tfrac{1}{4}) + (\text{SDEV Baseline Fill Delta [s] Threshold Exceeded})(\tfrac{1}{4}) + (\text{Max Delta Threshold Exceeded})*(\tfrac{1}{4}) = \text{Container Volume Determination} \qquad \text{Equation 2:}$$

For the Fill Time [s] Threshold, larger fill times are associated with the larger 900 g bibag container, and the value of 10.058 seconds exceeds the threshold value of 9.7 seconds and results in the Fill Time [s] Threshold value of 1 being assigned. For the Average Baseline Fill Delta [s] Threshold, larger values are associated with the larger 900 g bibag container, and the value of 5.892 seconds does not exceed the threshold value of 6 seconds and results in the Average Baseline Fill [s] Threshold value of −1 being assigned. For the SDEV Baseline Fill Delta [s] Threshold, larger values are associated with the larger 900 g bibag container, and the value of 1.2627 seconds does not exceed the threshold value of 3 seconds and results in the SDEV Baseline Fill [s] Threshold value of −1 being assigned. And for the Max Delta [s] Threshold, smaller values are associated with the larger 900 g bibag container, and the value of 32.399 seconds does not exceed the threshold value of 25 seconds and results in the Max Delta [s] Threshold value of −1 being assigned. With the number of fill parameters being assessed in the testing period set to 4, each threshold value is multiplied by ¼ to given equal weighting and results in the calculation below:

$$(1)(¼)+(-1)(¼)+(-1)(¼)+(-1)(¼)=-0.75 \qquad \text{Equation 3:}$$

As can be seen in equation 2, the fill parameters used for the volume determination are fill parameters 904, 908, 910, and 912. For this container, the initial fill time parameter 904 determined for the container exceeded the corresponding threshold, and thus was assigned a positive. However, the an average amount of time elapsed between each closing and reopening of valve 442 during baseline fill cycles 908, the standard deviation of the amount of time elapsed between each closing and reopening of valve 442 during baseline fill cycles 910, and the amount of time elapsed between the completion of the initial fill and the first valve 442 opening resultant of a baseline fill 912 determined for the container each did not exceed the corresponding parameter threshold, and, as a result were assigned a negative value. As can be seen in equation 3, the overall sum was negative, indicating that the volume of the container corresponds to a 650 g bibag, and not a 900 g bibag.

In order to improve accuracy of the determination of the volume of the container, rather than weighting each fill parameter equally, as is done using equation 1 above, in some implementations an algorithm that weights each of the fill parameters based on the predictive power of the respective fill parameters can be used. For example, some fill parameters are more strongly predictive to the volume of the container 104, such as the average amount of time between closing and reopening of valve 442 during baseline fill cycles 908, the standard deviation of the amounts of time between closing and reopening of valve 442 during baseline fill cycles 910, the amount of time elapsed between the completion of the initial fill procedure and the first valve 442 opening resultant of a baseline fill 912, and the presence of a second initial fill procedure (as indicated by max delta 2 fill parameter 914). In contrast, while still predictive of the container volume, some fill parameters were experimentally determined to be less predictive of the container volume when considering all combinations of prescription dialysate flow rate 924 and prescription bicarbonate setting 926, such as the total number of fills performed during the initial fill procedure 902, the amount of time during the initial fill procedure where valve 442 is open 904, and the average amount of time elapsed between each closing and reopening of valve 442 during the initial fill procedure 906. In order to improve accuracy of the container volume determination, an algorithm can be used that based on the prescription dialysate flow rate 924 and prescription bicarbonate setting 926 weights the more strongly predictive parameters (e.g., fill parameters 908-920) more heavily than the less predictive parameters (e.g., fill parameters 902-906).

Additionally, in some implementations the algorithm can be further refined to provide additional weighting to parameters that greatly exceed the threshold value, such as the value of 1.2627 seconds that was used to generate the value of −1 for the SDEV Baseline Fill Delta [s] Threshold value and the value of 32.399 seconds that was used to generate the value of −1 for the Max Delta [s] Threshold value above in equation 3, whereas the value of 5.892 seconds that was used to generate the value of −1 for the Average Baseline Fill Delta [s] Threshold value above in equation 3 could be given slightly less weight based on its close proximity to the threshold value of 6 seconds.

Referring back to FIG. 5, once the volume of the container 104 connected to the dialysis machine is determined and confirmed by the operator of the hemodialysis machine 106, the hemodialysis machine 106 determines an amount of time remaining before the concentrate will be depleted from the container 104 based on the determined container volume and the prescribed treatment parameters. The amount of time remaining before the concentrate will be depleted from the container 104 is displayed on the user interface 102 of the hemodialysis machine 106, and the operator can then view the amount of time remaining before the concentrate will be depleted from the container on the user interface 102 of the hemodialysis machine 106 (512). By being able to easily view of the amount of time remaining before the concentrate will be depleted from the container 104, the operator of the hemodialysis machine can make the necessary preparations to replace the depleted container 104 with a new container, if necessary. In addition, based on the amount of time remaining before the concentrate will be depleted from the container 104, in the event the machine or the operator adjusts one or more treatment parameters (e.g., the dialysate flow rate, the substitution fluid pump rate), as discussed in further detail below, a new estimated depletion time and remaining time can be calculated. In this way, one can think of the estimated depletion time and estimated remaining time as reactive to both manual and forced treatment parameter adjustments (e.g., resultant of the machine using an automated dialysate flowrate based on the blood pump rate, or resultant of a forced reduction in the substitution fluid pump rate due to high transmembrane pressure being detected).

FIG. 7 depicts a process 700 performed by the hemodialysis machine 106 to calculate the amount of time remaining before the concentrate will be depleted from the container 104. As described above, the processor 114 of the hemodialysis machine 106 receives treatment parameters for the dialysate treatment (702), including the dialysate flow rate, the bicarbonate solution concentration, the treatment time, and if applicable, the substitution fluid pump rate. Using the container volume determination process described in reference to FIG. 6, the processor 114 determines the volume of the container 104 coupled to the hemodialysis machine 106 (704).

Based on the determined container volume, the dialysate flow rate, the bicarbonate setting value, and if applicable, substitution fluid pump rate, the processor 114 automatically determines an estimate for the amount of time in which the concentrate will be depleted from the container (706). In some implementations, the hemodialysis machine 106 determines the depletion time using the following equation:

$$t(s, Q_d) = k_0 M_{bc} \frac{1000}{sQ_d}. \qquad \text{Equation 4}$$

Wherein t is the depletion time in minutes, s is the bicarbonate setting in mEq/g, $Q_d$ is the dialysate flow rate in mL/min, and $M_b$ is the bicarbonate mass in g. In some embodiments, the mass is 650 g or 900 g depending on the container volume inserted into the dialysate machine. In some examples, Equation 4 represents a temperature based coefficient and the values in FIG. 14 are used. Further details regarding Equation 4 can be found in U.S. Pat. No. 11,123,464. As noted above, the content of U.S. Pat. No. 11,123,464 is hereby incorporated by reference in entirety.

In some implementations, the depletion time is determined using a table of depletion times experimentally determined for containers of the same volume by testing the containers of the same volume using the same dialysate flow rate and the bicarbonate setting value as that used to test the container 104. For example, FIG. 14 depicts an example table 1400 of depletion times determined for 900 g bibags and 650 g bibags. The table 1400 can be used to identify approximate depletion times 1402 for containers with known volumes 1404. For instance, the table 1400 can used to determine the amount of time in which the concentrate will be depleted from the container 104 during a particular dialysis treatment by first identifying the portion 1404 of the table 1400 that corresponds to the relevant container size, and pinpointing the depletion time 1402 within the relevant portion 1404 of the table that corresponds to the same level of bicarbonate and the same dialysate flow rate and if applicable substitution fluid pump rate as was used for testing the container 104.

Referring briefly again to FIGS. 3 and 7, the hemodialysis machine 106 can display the determined depletion time 308 on the user interface 300 of the hemodialysis machine 106 (708).

Still referring to FIG. 7, based on the total depletion time determined for the container, the hemodialysis machine 106 further determines an amount of time remaining before the concentrate will be depleted from the container (710). For example, the amount of the time remaining before the concentrate will be depleted from the container is determined by subtracting the amount of time that has elapsed since the attachment of the container from the total depletion time calculated for the container. Upon calculation of the time remaining before the concentrate will be depleted from the container the hemodialysis machine displays the amount of time remaining before the concentrate will be depleted from the container 310 on the user interface 300 of the hemodialysis machine 106, as depicted in FIG. 3 (716).

The hemodialysis machine then uses processor 114 to calculate and display the total estimated bicarbonate containers required (344) based on the estimated depletion time, total treatment time, remaining treatment time, and prescription dialysate flow rate, prescription bicarbonate concentration setting, and if applicable the substitution fluid pump rate (730). The total estimated bicarbonate containers would assess the relevant machine parameters to recommend container replacements of the appropriate size as to both minimize the number of containers used and optimize the utilization of the used containers as much as practical.

In some implementations, as the treatment progresses, the estimated remaining time 310 decrements, and the hemodialysis machine 106 uses processor 114 to compare the amount of time remaining before the bicarbonate will be depleted from the container to a threshold amount of time 332 (712), and, if the calculated amount of time remaining before the bicarbonate concentrate will be depleted from the container is less than or equal to the threshold amount of time 332, the hemodialysis machine generates an alert (714) to notify the operator of the dialysis machine that the container will soon require replacement. For example, in some implementations, the adjustable threshold time 332 is set to 20% of the estimated depletion time, and the hemodialysis machine 106 is configured to generate an alert whenever the amount of time remaining before the bicarbonate will be depleted from the container is determined to be less than or equal to this threshold time 332. In some implementations, the alert generated by the hemodialysis machine 106 is a visual alert indicating the estimated time remaining before depletion is below a threshold (e.g., displayed on the user interface). In some implementations, the alert generated by the hemodialysis machine 106 is an auditory alert emitted by a speaker 118 of the hemodialysis machine 106 indicating the estimated time remaining before depletion is below a threshold.

In some implementations, the temperature of the water being provided to the container 104 is dynamically adjusted by the hemodialysis machine 106 during treatment in order to improve utilization of the bicarbonate within the container 104 and, as a result, extend the depletion time of the container 104. In addition, in some implementations, the pressure within the container 104 can be dynamically adjusted by the hemodialysis machine 106 during treatment in order to improve utilization of the bicarbonate within the container 104 and, as a result, extend the depletion time of the container 104. Adjusting the temperature of the water provided to the container 104 or the pressure within the container 104 may be particularly useful in increasing the utilization rates and depletion time of containers with a larger volume, such as 900 g bibags. In some implementations, adjustment of the temperature of the water provided to the container 104 or the pressure within the container 104 would generate a larger depletion time is determined. In some examples, the machine increases the pressure in the container and/or increases the temperature of RO water introduced into the container over time to accelerate the dissolving of the powdered bicarbonate into solution.

As the hemodialysis treatment proceeds, the hemodialysis machine 106 decrements the amount of time remaining before the bicarbonate concentrate will be depleted from the container 104 (710) and compares the updated amount of time remaining before the concentrate will be depleted to the threshold amount of time (712).

In some implementations, if one or more of updated treatment parameters are received during treatment (718), such as an updated dialysate flow rate, updated substitution fluid pump rate, or an updated bicarbonate concentrate setting, the hemodialysis machine 106 again calculates (706) and displays (708) an updated depletion time that is determined based on the updated treatment parameters, and calculates an updated amount of time remaining before the concentrate will be depleted (710) that is determined based on the updated depletion time which is then displayed on the user interface (716). When the updated treatment parameters are resultant of changes by the operator, the recalculation of the estimated depletion time and remaining treatment time would be immediate; however, in the event of automated adjustment to the dialysate flowrate and/or substitution fluid pump rate (e.g., such as the substitution fluid pump temporarily stopping resultant of an arterial pressure alarm or an automatic dialysate flowrate resultant of a change of the blood pump rate), the update would occur after a period of 2-3 minutes after completion of any automated adjustments to ensure that the updated times are truly reflective of the changes to the dialysate flow rate and/or substitution fluid pump rate that had occurred and to reduce (e.g., minimize) repetitive updates.

Upon completion of the updates to the treatment parameters dialysate flow rate, bicarbonate concentration setting, and/or substitution fluid pump rate, and in the event of adjustments to the total treatment time (734), the recalculated estimated depletion time 308, estimated time remaining (310), and total treatment time are used by processor 114 to as needed adapt the total estimated bicarb containers required (344) based on the estimated (730). A determination is made if the recommendation has changed, and if so, the machine shall generate an alert to the operator (732) to allow for them to have sufficient time to prepare as may be required.

In addition, if the container 104 is replaced with a new container during treatment (e.g., because the original container 104 was depleted before the end of treatment), the hemodialysis machine 106 returns to step 704 to perform a volume determination for the new container, calculate a corresponding depletion time 706, display the new depletion time 708, calculate the estimated remaining time 710, display the estimated remaining time 716, calculate and display a new estimated number of bicarbonate containers required to complete the treatment 730, and alert the operator if there is a relevant change 732, and again begin the process of decrementing the estimated remaining time and comparing to an alert threshold 712. For example, as noted above, there are sensors on the door that can tell when a bag is attached and the bag door is closed or open.

Additionally, upon container replacement, a utilization percentage for the previously attached container is calculated and displayed using the following formula:

$$Util\ \% = 100 * \frac{(Est.\ \text{Depletion Time}) - (Est.\ \text{Remaining } Time_{At\ Time\ of\ Removal})}{(Est.\ \text{Depletion Time})} \qquad \text{Equation 5}$$

where Est. Depletion Time is the estimated depletion time calculated for the previous container at the time of container removal, Est. Remaining Time$_{At\ Time\ of\ Removal}$ is the estimated remaining time calculated for the previous container at the time of container removal, and Util % is the utilization percentage for the previous container.

Over the course of treatment, each container used is stored by the machine, with a respective date and time of connection to the machine, the determined size resultant of the testing period, and the respective utilization percentage. This logged information will be available for later viewing or upload to provide a better understanding of the number and size of containers used on the machine over the week or month, along with respective utilization percentages to allow for an assessment of the utilization.

While certain embodiments have been described above, other embodiments are possible.

For example, while the container 104 has been described as corresponding to either a 650 g bibag or a 900 g bibag, other container sizes can be coupled to the hemodialysis machine 106 and used for hemodialysis treatment, and the volume and estimated depletion time of each of these containers can be automatically determined by the hemodialysis machine 106.

Further, while the container 104 has been described as containing bicarbonate for forming bicarbonate solution, the container can include other substances. In some implementations, the container 104 contains an acid compound that is used to form an acid solution that can be used to form dialysate.

In addition, while the hemodialysis system 100 has only been described as having a single container 104 attached to the hemodialysis machine 106, in some implementations, two or more containers are attached to the hemodialysis machine to generate a corresponding number of fluid solutions, and the volume and estimated depletion time of each of these containers can be automatically determined by the hemodialysis machine 106. For example, when dried acid is used to form an acid solution, the machine 106 can independently determine the volume of two containers that are used to form the acid solution.

While the container 104 has been primarily described as being coupled to a hemodialysis machine 106, the container 104 can also be used for generating dialysate solution and substitution fluid solution during other blood treatments including, hemofiltration (HF) treatment, and hemodiafiltration (HDF) treatment, and generally any blood treatment.

In some implementations, the priming of the circuit at the start of treatment and reinfusion of blood to the patient at the end of treatment is achieved through use of substitution fluid which would result in update of the estimated depletion time and estimated remaining time based on the substitution fluid pump rate and duration of time the substitution fluid pump was ran.

Implementations of the subject matter and the functional operations described above can be implemented in various types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine-readable storage device, a machine-readable storage substrate, a memory device, a composition of matter effecting a machine-readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments have been described. Nevertheless, it will be understood that various modifications may be made without departing from the spirit and scope of the disclosure. Accordingly, other embodiments are within the scope of the following claims.

What is claimed is:

1. A method comprising:
receiving, by a processor of a dialysis machine, a dialysate flow rate, a bicarbonate setting value, a signal from a pressure sensor configured to measure a pressure within a container containing a concentrate as fluid flows from a point upstream of the pressure sensor to the container, and a signal indicating a state of a fill valve upstream of the container as open or closed;
determining, based on the signal received from the pressure sensor and the state of the fill valve during a testing period, fill parameters comprising:
an amount of time elapsed between a completion of an initial fill of the container and an initiation of a first baseline fill of the container during the testing period;
an average of amounts of time elapsed between each fill valve closing and reopening during baseline fill cycles of the container during the testing period; and
a standard deviation of the amounts of time elapsed between each fill valve closing and reopening during the baseline fill cycles of the container during the testing period;
determining a volume of the container based on at least two of the fill parameters;
determining a depletion time in which the concentrate will be depleted from the container based on the volume of the container, the dialysate flow rate, and the bicarbonate setting value;
determining, based on the depletion time, an amount of time remaining before the concentrate will be depleted from the container; and
causing the dialysis machine to indicate the amount of time remaining before the concentrate will be depleted from the container to a user.

2. The method of claim 1, wherein determining the amount of time elapsed between the completion of the initial fill of the container and the initiation of the first baseline fill of the container comprises determining an amount of time elapsed between a time at which the pressure sensor detects that an initial fill completion pressure threshold has been established and a time at which the pressure sensor detects a baseline fill pressure threshold has been established during the testing period.

3. The method of claim 1, wherein determining the average of the amounts of time elapsed between each fill valve closing and reopening during the baseline fill cycles of the container during the testing period comprises determining, based on the signal indicating the state of the fill valve, an average of amounts of time elapsed between each detection of the state of the fill valve as being closed and subsequently opened after detecting by the pressure sensor that a baseline fill pressure threshold has been established during the testing period.

4. The method of claim 1, wherein determining the standard deviation of the amounts of time elapsed between each fill valve closing and reopening during the baseline fill cycles of the container during the testing period comprises determining, based on the signal indicating the state of the fill valve, a standard deviation of amounts of time elapsed between each detection of the state of the fill valve as being closed and subsequently opened after detecting by the pressure sensor that a baseline fill pressure threshold has been established during the testing period.

5. The method of claim 1, wherein the fill parameters further comprise an amount of time elapsed during the initial fill of the container where the state of the fill valve is open.

6. The method of claim 5, wherein determining the amount of time elapsed during the initial fill of the container where the state of the fill valve is open comprises determining, based on the signal indicating the state of the fill valve, an amount of time elapsed between a time corresponding to an initial flow of fluid from the point upstream of the pressure sensor to the container and a time at which the pressure sensor detects that an initial fill completion pressure threshold has been established.

7. The method of claim 1, wherein the fill parameters further comprise an average of the amounts of time elapsed between each fill valve closing and reopening of a plurality of fill cycles performed during the initial fill of the container.

8. The method of claim 7, wherein determining the average of the amounts of time elapsed between each fill valve closing and reopening of the plurality of fill cycles performed during the initial fill of the container comprises determining, based on the signal indicating the state of the fill valve, an average of an amount of time elapsed between each closing of the fill valve and each subsequent opening of the fill valve during the initial fill of the container.

9. The method of claim 1, wherein the fill parameters further comprise a number of fill cycles performed during the initial fill of the container.

10. The method of claim 9, wherein determining the number of fill cycles performed during the initial fill of the container comprises determining, based on the signal indicating the state of the fill valve, a number of times the fill valve is opened before an initial fill completion pressure threshold has been established.

11. The method of claim 1, wherein the fill parameters further comprise a rate of change of pressure measured by the pressure sensor between a time at which a pressure threshold of interest is established and a time at which a baseline fill pressure threshold is established.

12. The method of claim 1, wherein the fill parameters further comprise a minimum rate of change of pressure measured by the pressure sensor between a time at which a pressure threshold of interest is established and a time at which a baseline fill pressure threshold is established.

13. The method of claim 12, wherein the pressure threshold of interest is established when a rate of decrease of pressure detected by the pressure sensor exceeds a threshold after an initial fill completion pressure threshold has been established.

14. The method of claim 1, wherein the fill parameters further comprise a rate of change of pressure measured by the pressure sensor during a time period immediately before a baseline fill pressure threshold has been established.

15. The method of claim 1, wherein:
the initial fill is triggered when the pressure sensor detects that the pressure within the container is below an initial fill trigger pressure threshold;
the initial fill is completed when the pressure sensor detects that the pressure within the container corresponds to an initial fill completion pressure threshold and is maintained for a predetermined amount of time;

the first baseline fill is triggered when the pressure sensor detects that the pressure within the container is below a baseline fill pressure threshold after the initial fill is completed; and the initial fill trigger pressure threshold being lower than the baseline fill pressure threshold and the baseline fill pressure threshold being lower than the initial fill completion pressure threshold.

16. The method of claim 15, wherein the initial fill trigger pressure threshold is 70 mmHg, the baseline fill pressure threshold is 90 mmHg, and the initial fill completion pressure threshold is 150 mmHg.

17. The method of claim 15, wherein the fill parameters further comprise detection of a second initial fill of the container during the testing period.

18. The method of claim 17, wherein detecting the second initial fill of the container during the testing period comprises determining, based on signals received from the pressure sensor, that the initial fill trigger pressure threshold has been established after the initial fill completion pressure threshold has been established during the testing period.

19. The method of claim 1, wherein determining the volume of the container based on at least two of the fill parameters comprises comparing each of the at least two of the fill parameters to a corresponding threshold for a particular container volume.

20. The method of claim 19, wherein determining the volume of the container based on at least two of the fill parameters comprises calculating a weighted average based on the comparing of each of the at least two of the fill parameters to the corresponding threshold.

21. The method of claim 1, further comprising:
receiving a total treatment time and a number of container volumes supported by the dialysis machine;
comparing the depletion time in which the concentrate will be depleted from the container with the total treatment time;
determining a minimal number of containers required to complete a treatment based on (i) the comparison of the depletion time with the total treatment time and (ii) the number of container volumes supported by the dialysis machine; and
causing the dialysis machine to indicate (i) the depletion time and (ii) the minimal number of containers required to complete the treatment.

22. A system comprising:
a container containing bicarbonate and configured to receive RO water and deliver bicarbonate solution at a prescribed rate;
a dialysis machine comprising:
a pressure sensor configured to detect fluid pressure within the container;
a dialysate fluid circuit configured to deliver dialysate at a prescribed dialysate flow rate;
a fill valve configured to open and close to control a flow of the RO water into the container; and
a data processing apparatus configured to receive signals from the pressure sensor, a signal indicating the prescribed dialysate flow rate, a signal indicating a prescribed bicarbonate setting, and a signal indicating a state of the fill valve as open or closed, the data processing apparatus configured to:
based on the signals received from the pressure sensor and the signals indicating the state of the fill valve, determining fill parameters comprising:

an amount of time elapsed between a completion of an initial fill of the container and an initiation of a first baseline fill of the container during a testing period;
an average of amounts of time elapsed between each fill valve closing and reopening during baseline fill cycles of the container during the testing period; and
a standard deviation of the amounts of time elapsed between each fill valve closing and reopening during the baseline fill cycles of the container during the testing period;
determining a volume of the container based on at least two of the fill parameters;
determining a depletion time in which the bicarbonate will be depleted from the container based on the volume of the container, the prescribed dialysate flow rate, and the prescribed bicarbonate setting;
determining, based on the depletion time, an amount of time remaining before the bicarbonate will be depleted from the container; and
causing the dialysis machine indicate the amount of time remaining before the bicarbonate will be depleted from the container to a user.

23. The system of claim 22, further comprising a fluid line coupled to the container containing the bicarbonate, the fluid line being configured to deliver the RO water to the container via a fill valve for mixing with a portion of the bicarbonate to produce a solution of bicarbonate.

24. The system of claim 22, further comprising a user interface configured to prompt a user to input a prescription comprising the prescribed dialysate flow rate and the prescribed bicarbonate setting.

25. The system of claim 22, wherein the data processing apparatus is configured to notify the user when the amount of time remaining before the bicarbonate will be depleted from the container is less than a predetermined amount of time.

26. The system of claim 22, wherein:
the data processing apparatus is configured to cause the dialysis machine to perform the initial fill when the pressure sensor detects that the fluid pressure within the container is below an initial fill trigger pressure threshold;
the data processing apparatus is configured to cause the dialysis machine to complete the initial fill when the pressure sensor detects the pressure within the container meets an initial fill completion pressure threshold; and
the data processing apparatus is configured to cause the dialysis machine to perform the baseline fill when the pressure sensor detects that the fluid pressure within the container is below a baseline fill pressure threshold after the completion on the initial fill, the initial fill trigger pressure threshold being lower than the baseline fill pressure threshold and the baseline fill pressure threshold being lower than the initial fill completion pressure threshold.

27. The system of claim 26, wherein the initial fill trigger pressure threshold is 70 mmHg, the baseline fill pressure threshold is 90 mmHg, and the initial fill completion pressure threshold is 150 mmHg.

28. The system of claim 22, wherein the fill parameters further comprise an amount of time elapsed during the initial fill of the container where the state of the fill valve is open.

29. The system of claim 22, wherein the fill parameters further comprise an average of the amounts of time elapsed between each fill valve closing and reopening during a plurality of fill cycles performed during the initial fill of the container.

30. The system of claim 22, wherein the fill parameters further comprise a number of fill cycles performed during the initial fill of the container.

\* \* \* \* \*